US008431529B2

(12) United States Patent
Pellecchia

(10) Patent No.: US 8,431,529 B2
(45) Date of Patent: *Apr. 30, 2013

(54) BI-DENTATE COMPOUNDS AS KINASE INHIBITORS

(75) Inventor: Maurizio Pellecchia, San Diego, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 211 days.

This patent is subject to a terminal disclaimer.

(21) Appl. No.: 12/970,813

(22) Filed: Dec. 16, 2010

(65) Prior Publication Data

US 2011/0172164 A1    Jul. 14, 2011

Related U.S. Application Data

(63) Continuation-in-part of application No. 12/184,208, filed on Jul. 31, 2008, now Pat. No. 7,919,581.

(60) Provisional application No. 60/962,778, filed on Jul. 31, 2007.

(51) Int. Cl.
*A01N 37/18* (2006.01)
*A61K 38/04* (2006.01)

(52) U.S. Cl.
USPC .......................................................... 514/2.9

(58) Field of Classification Search .................. None
See application file for complete search history.

(56) References Cited

U.S. PATENT DOCUMENTS

| 6,753,313 | B1 | 6/2004 | Dasseux et al. | |
|---|---|---|---|---|
| 7,919,581 | B2 * | 4/2011 | Pellechia | 530/328 |
| 2005/0019824 | A1 | 1/2005 | Alderson et al. | |
| 2005/0026840 | A1 | 2/2005 | Livnah et al. | |
| 2007/0083334 | A1 | 4/2007 | Mintz et al. | |
| 2007/0111926 | A1 | 5/2007 | Zundel et al. | |
| 2007/0161648 | A1 | 7/2007 | Hughes et al. | |
| 2009/0054348 | A1 | 2/2009 | Pellecchia | |
| 2010/0240720 | A1 * | 9/2010 | Pellecchia | 514/365 |

FOREIGN PATENT DOCUMENTS

WO    WO 2007/016777 A1    2/2007

* cited by examiner

*Primary Examiner* — Marcela M Cordero Garcia
(74) *Attorney, Agent, or Firm* — DLA Piper LLP (US)

(57) ABSTRACT

The present disclosure provides compound having the general structure A or pharmaceutically acceptable salts thereof:

Het-L-P    (A)

wherein Het is an aromatic moiety comprising a heterocyclic structure mimicking ATP, P is a docking site derived peptide or a docking site peptide mimetic, and L is a linking moiety, wherein L links the ATP mimetic to the docking site peptide moiety. The compounds having the general structure A can serve as inhibitors of kinases, such as the kinases JNK, Erk and p38.

10 Claims, 8 Drawing Sheets

Log [Ac-RPTTLNLGG-OH] μM

Log [Compound I] nM

Log [Product 8] μM

Log [Compound I] μM

Compound I against p38

Compound IV against p38

SEQUENCE LISTING

<160> NUMBER OF SEQ ID NOS: 18

<210> SEQ ID NO 1
<211> LENGTH: 9
<212> TYPE: PRT
<213> ORGANISM: Artificial sequence
<220> FEATURE:
<223> OTHER INFORMATION: Synthetic construct

<400> SEQUENCE: 1

Arg Pro Thr Thr Leu Asn Leu Gly Gly
1               5

<210> SEQ ID NO 2
<211> LENGTH: 8
<212> TYPE: PRT

```
<213> ORGANISM: Artificial sequence
<220> FEATURE:
<223> OTHER INFORMATION: Synthetic construct

<400> SEQUENCE: 2

Pro Thr Thr Leu Asn Leu Gly Gly
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic construct

<400> SEQUENCE: 3

Leu Asn Leu Gly Gly
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic construct

<400> SEQUENCE: 4

Arg Pro Thr Thr Leu Asn Leu
1               5

<210> SEQ ID NO 5
<211> LENGTH: 21
<212> TYPE: PRT
<213> ORGANISM: Artificial sequence
<220> FEATURE:
<223> OTHER INFORMATION: Synthetic construct

<400> SEQUENCE: 5

Gly Arg Lys Lys Arg Arg Gln Arg Arg Gly Gly Arg Pro Thr Thr
1               5                   10                  15

Leu Asn Leu Gly Gly
            20

<210> SEQ ID NO 6
<211> LENGTH: 21
<212> TYPE: PRT
<213> ORGANISM: Artificial sequence
<220> FEATURE:
<223> OTHER INFORMATION: Synthetic construct

<400> SEQUENCE: 6

Gly Gly Leu Asn Leu Thr Thr Pro Arg Gly Gly Arg Arg Gln Arg
1               5                   10                  15

Arg Lys Lys Arg Gly
            20

<210> SEQ ID NO 7
<211> LENGTH: 10
<212> TYPE: PRT
<213> ORGANISM: Artificial sequence
<220> FEATURE:
<223> OTHER INFORMATION: Synthetic construct

<400> SEQUENCE: 7

Gly Arg Pro Thr Thr Leu Asn Leu Gly Gly
1               5                   10
```

```
<210> SEQ ID NO 8
<211> LENGTH: 21
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (14)..(21)
<223> OTHER INFORMATION: Xaa can be any naturally occurring amino acid

<400> SEQUENCE: 8

Xaa Xaa Xaa Xaa Xaa Xaa Xaa Xaa Leu Asn Leu Gly Gly Xaa Xaa Xaa
1               5                   10                  15

Xaa Xaa Xaa Xaa Xaa
            20

<210> SEQ ID NO 9
<211> LENGTH: 19
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (12)..(19)
<223> OTHER INFORMATION: Xaa can be any naturally occurring amino acid

<400> SEQUENCE: 9

Xaa Xaa Xaa Xaa Xaa Xaa Xaa Xaa Leu Asn Leu Xaa Xaa Xaa Xaa Xaa
1               5                   10                  15

Xaa Xaa Xaa

<210> SEQ ID NO 10
<211> LENGTH: 6
<212> TYPE: PRT
<213> ORGANISM: Artificial sequence
<220> FEATURE:
<223> OTHER INFORMATION: Synthetic construct

<400> SEQUENCE: 10

Pro Thr Thr Leu Asn Leu
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic construct

<400> SEQUENCE: 11

Gly Gly Leu Asn Leu Thr Thr Pro Arg
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic construct
```

```
<400> SEQUENCE: 12

Gly Gly Leu Asn Leu Thr Thr Pro
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic construct

<400> SEQUENCE: 13

Gly Gly Leu Asn Leu
1               5

<210> SEQ ID NO 14
<211> LENGTH: 7
<212> TYPE: PRT
<213> ORGANISM: Artificial sequence
<220> FEATURE:
<223> OTHER INFORMATION: Synthetic construct

<400> SEQUENCE: 14

Leu Asn Leu Thr Thr Pro Arg
1               5

<210> SEQ ID NO 15
<211> LENGTH: 6
<212> TYPE: PRT
<213> ORGANISM: Artificial sequence
<220> FEATURE:
<223> OTHER INFORMATION: Synthetic construct

<400> SEQUENCE: 15

Leu Asn Leu Thr Thr Pro
1               5

<210> SEQ ID NO 16
<211> LENGTH: 11
<212> TYPE: PRT
<213> ORGANISM: Artificial sequence
<220> FEATURE:
<223> OTHER INFORMATION: Synthetic construct

<400> SEQUENCE: 16

Arg Pro Lys Arg Pro Thr Thr Leu Asn Leu Phe
1               5                   10

<210> SEQ ID NO 17
<211> LENGTH: 32
<212> TYPE: PRT
<213> ORGANISM: Artificial Sequence
<220> FEATURE:
<223> OTHER INFORMATION: Synthetic construct

<400> SEQUENCE: 17

Thr Asp Gln Ser Arg Pro Val Gln Pro Phe Leu Asn Leu Thr Thr Pro
1               5                   10                  15

Arg Arg Pro Arg Pro Pro Arg Arg Gln Arg Arg Lys Lys Arg Gly
            20                  25                  30

<210> SEQ ID NO 18
<211> LENGTH: 12
<212> TYPE: PRT
<213> ORGANISM: Artificial Sequence
<220> FEATURE:
```

```
<223> OTHER INFORMATION: Synthetic construct

<400> SEQUENCE: 18

Lys Arg Pro Lys Arg Pro Thr Thr Leu Asn Leu Phe
1               5                   10
```

BI-DENTATE COMPOUNDS AS KINASE INHIBITORS

CROSS-REFERENCE TO RELATED APPLICATIONS

This application is a continuation-in-part application of U.S. patent application Ser. No. 12/184,208 filed Jul. 31, 2008, now U.S. Pat. No. 7,919,581 which claims priority under 35 U.S.C. §119(e) to U.S. Provisional Patent Application Ser. No. 60/962,778 filed Jul. 31, 2007, which are herein incorporated by reference in their entirety.

GRANT INFORMATION

This invention was made with government support under grant numbers R21 DK073274and R24DK080263 awarded by the National Institutes of Health, NIDDK branch. The government has certain rights in the invention.

BACKGROUND

1. Field of the Disclosure

The present disclosure relates generally to compounds useful for the inhibition of kinases, and more specifically, to bi-dentate compounds that are useful as kinase inhibitors.

2. Background Information

Protein kinases are families of enzymes that catalyze the phosphorylation of specific residues in proteins, and may be broadly classified into tyrosine or serine/threonine kinases based on the amino acids phosphorylated. This covalent post-translational modification is a pivotal component of normal cellular communication and maintenance of homeostasis.

There is a body of evidence linking kinase misregulation, dysregulation and mutation to a variety of disorders including cancer, diabetes, ocular diseases and other indications. Inappropriate kinase activity triggers a variety of biological cellular responses relating to cell growth, cell differentiation, survival, apoptosis, mitogenesis, cell cycle control, and cell mobility implicated in the above-mentioned and other diseases.

Accordingly, inhibiting kinases, such as C-Jun N-terminal kinase (JNK), is one method of treating various diseases, disorders and pathologies associated with kinases. Previously, some compounds that can be useful as inhibitors of certain kinases, and which target the ATP binding site of the protein, have been identified and synthesized.

While some JNK-interacting peptides (JIP) and JIP mimics capable of doing so have been described previously, no compounds have been reported that are capable of targeting and inhibiting JNK kinase binding to the docking site (JIP site) for the substrate or scaffolding proteins and the ATP binding site at the same time.

SUMMARY OF THE DISCLOSURE

Currently, there is a need for identifying potent and selective agents for the treatment of various diseases, disorders and pathologies, such as tumors, as well as for the pharmaceutical compositions including such agents. Such agents can be based on inhibition of certain kinases, such as JNK kinase.

In addition a few JNK-interacting peptides (JIP) and JIP mimics capable of inhibiting JNK have been also described. These JIP mimics tend to be specific but with modest affinities. In the present disclosure, compounds are described for the first time that are capable of targeting and inhibiting JNK kinase by binding to both the docking site (JIP site) for the substrate or scaffolding proteins and the ATP site. These compounds are thus both potent and specific.

According to embodiments of he present disclosure, there are provided compounds having the general structure A or pharmaceutically acceptable salts thereof:

Het-L-P (A)

wherein Het is an aromatic moiety comprising a heterocyclic structure, P is a peptide moiety comprising a peptide or a polypeptide, and L is a linking moiety, wherein L links the aromatic moiety to the peptide moiety.

In some embodiments of the present disclosure, in the compounds having the general structure A shown above, the aromatic moiety Het comprises a heterocyclic structure that includes a derivative of indazole. For example, the aromatic moiety Het comprises the following, indazole-based, moiety:

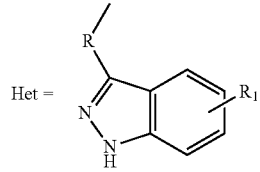

wherein R is an aromatic substituent, and $R_1$ is hydrogen or a substituent selected from the group consisting of a straight-chained alkyl, a branched alkyl, and a halogen, and wherein the moiety Het is connected to the linking moiety via the aromatic substituent R.

According to some embodiments of the present disclosure, compounds are provided having the formulae I-VIII, wherein the compounds I-VII comprise SEQ ID NO'S 1 to 7 and compound VIII comprises SEQ ID NO:1 accordingly:

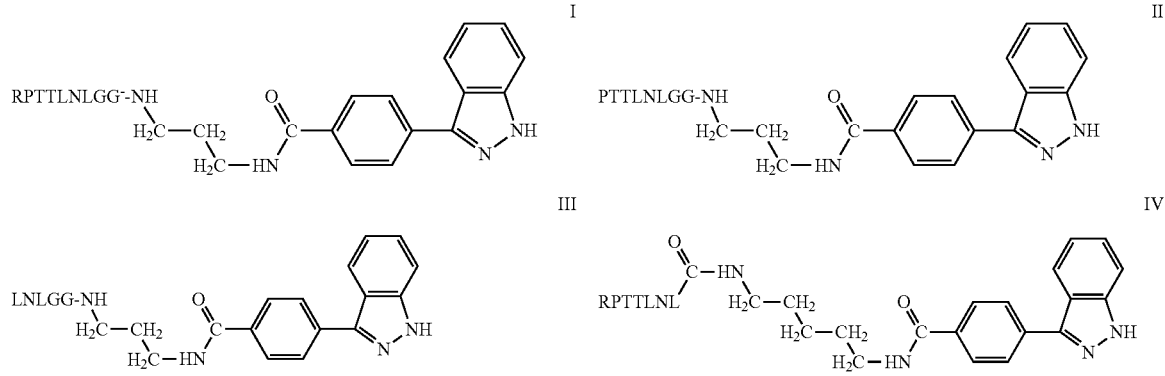

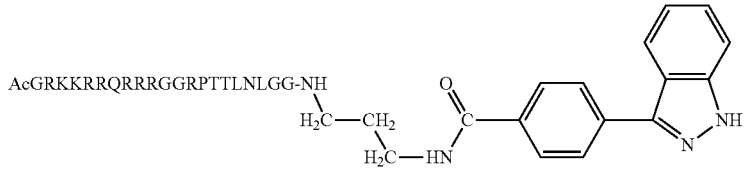

V

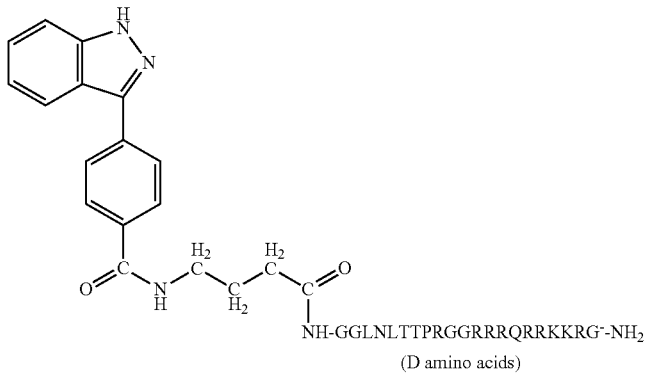

VI

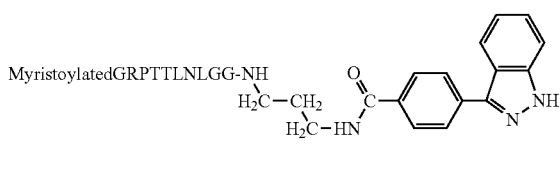

VII

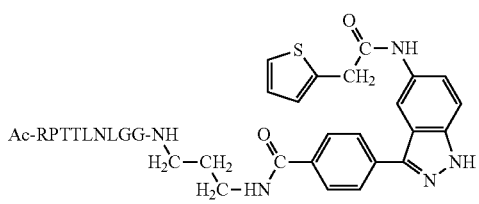

VIII

According to other embodiments of the present disclosure, pharmaceutical compositions are provided for the treatment of various disorders, diseases, and pathologies, such as cancer, diabetes, and neurological disorders, the compositions comprising a compound having the general structure A, and a pharmaceutically acceptable carrier.

According to other embodiments of the present disclosure, methods for the treatment of various disorders, diseases, and pathologies, such as cancer, diabetes and neurological disorders, are provided, the methods comprising administering to a subject in need thereof a pharmacologically effective dose of a pharmaceutical composition comprising a compound having the general structure A.

According to other embodiments of the present disclosure, a compound of formula I is provided:

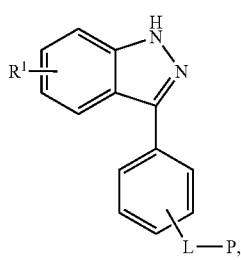

(I)

or a pharmaceutically acceptable salt thereof, wherein:

$R^1$ is hydrogen, straight-chained alkyl, branched alkyl, halogen, nitro, or $NHC(O)CH_2C_4H_3S$;

L is a linking moiety selected from the group consisting of (a) —CONH—$(CH_2)_n$—NH—, (b) —CONH—$(CH_2)_n$—NHCO—, (c) —CONH—$(CH_2)_n$—CONH—, (d) —$(CH_2)_n$—, (e) —O—$(CH_2)_n$—O—, (f) —$(CH_2)$-phenylene-, and (h) —$NHSO_2$—$(CH_2)_n$CONH—, wherein n is an integer between 2 and 8; and P is a peptide consisting of the sequence selected from the group consisting of RPTTLNL (SEQ ID NO:4), N-myristoilated RPTTLNL (SEQ ID NO:4), and GGLNLTTPRGGRRRQRRKKRG (SEQ ID NO:6).

According to other embodiments of the present disclosure, a compound of formula I is provided, wherein the compound binds to a JNK kinase docking site.

According to other embodiments of the present disclosure, a compound of formula I is provided, wherein L is —CONH—$(CH_2)_n$—NH—; and P is a peptide consisting of the sequence selected from RPTTLNL (SEQ ID NO:4), and GGLNLTTPRGGRRRQRRKKRG (SEQ ID NO:6).

According to other embodiments of the present disclosure, a compound of formula I is provided, wherein $R^1$ is hydrogen or straight chain alkyl; and L is —CONH—$(CH_2)_3$—NH—.

According to other embodiments of the present disclosure, a compound of formula I is provided, wherein the compound of formula I has formula II:

(SEQ ID NO: 4)

(II)

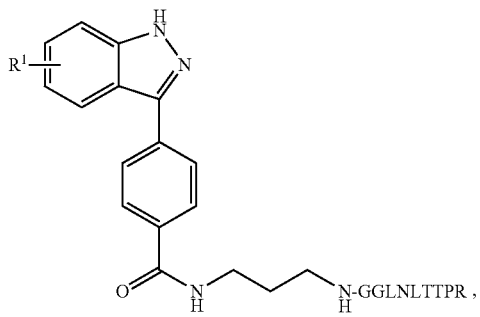

or wherein the compound of formula I has formula III:

(SEQ ID NO: 6 (D amino acids))

(III)

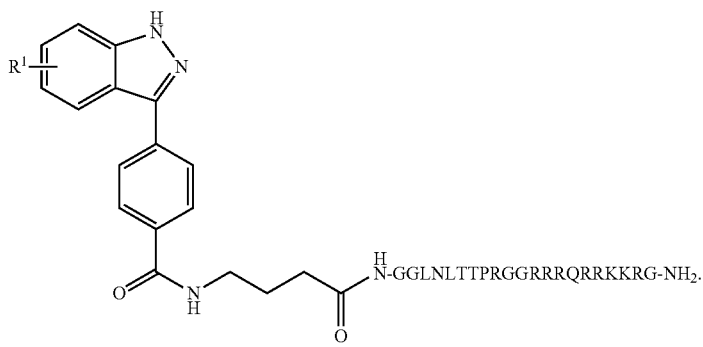

According to other embodiments of the present disclosure, pharmaceutical compositions are provided, including the compound of formula I or the compound of formula II or formula III, and a pharmaceutically acceptable carrier.

According to other embodiments of the present disclosure, pharmaceutical compositions are provided, including the compound of formula I or the compound of formula II or formula III, and a pharmaceutically acceptable carrier, further including an additional compound selected from the group consisting of: (1) an estrogen receptor modulator, (2) an androgen receptor modulator, (3) retinoid receptor modulator, (4) a cytotoxic agent, (5) an antiproliferative agent, (6) a prenyl-protein transferase inhibitor, (7) an HMG-CoA reductase inhibitor, (8) an HIV protease inhibitor, (9) a reverse transcriptase inhibitor, (10) another angiogenesis inhibitor, and (11) a PPAR-gamma agonist.

According to other embodiments of the present disclosure, methods for treating retina vascularization are provided, including administering to a subject a therapeutically effective amount of a pharmaceutical composition of the compound of formula I, formula II or formula III.

According to other embodiments of the present disclosure, methods for treating diabetic retinopathy are provided, including administering to a subject a therapeutically effective amount of a pharmaceutical composition of the compound of formula I, formula II or formula III.

According to other embodiments of the present disclosure, kits are provided, including a packaging material and a pharmaceutical composition of formula I, formula II or formula III contained within the packaging material, wherein the packaging material includes a label, which indicates that the composition can be used for treating a disorder, disease, or pathology in a subject in need thereof.

DETAILED DESCRIPTION OF THE DISCLOSURE

Definitions

Figure 1A:
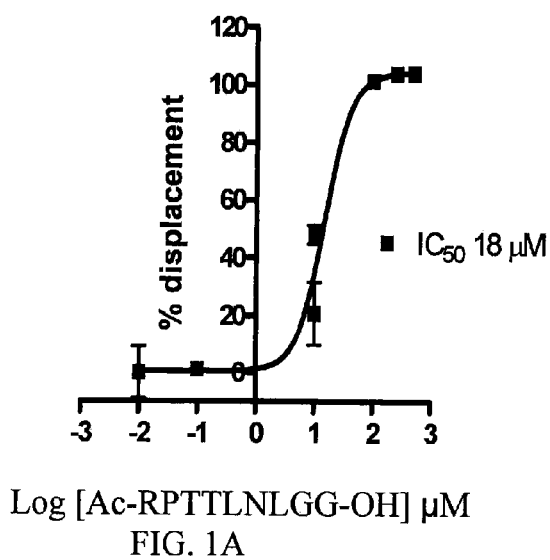
FIG. 1A illustrates kinase inhibition by the peptide Ac-RPTTLNLGG-OH (SEQ ID NO:1), which illustration is provided for the purposes of comparison.

As used herein, the term "alkyl" refers to either substituted or unsubstituted $C_1$-$C_{10}$ straight chain saturated aliphatic hydrocarbon groups, substituted and unsubstituted $C_2$-$C_{10}$ straight chain unsaturated aliphatic hydrocarbon groups, substituted and unsubstituted $C_4$-$C_{10}$ branched saturated aliphatic hydrocarbon groups, substituted and unsubstituted $C_4$-$C_{10}$ branched unsaturated aliphatic hydrocarbon groups, substituted and unsubstituted $C_3$-$C_8$ cyclic saturated aliphatic hydrocarbon groups, substituted and unsubstituted $C_5$-$C_8$ cyclic unsaturated aliphatic hydrocarbon groups having the specified number of carbon atoms. For example, the definition of "alkyl" shall include but is not limited to: methyl, ethyl, propyl, butyl, pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl, isobutyl, tert-butyl, sec-butyl, isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like.

As used herein, alkyl substituents are independently selected from the group consisting of halogen, —OH, —SH, —NH$_2$, —CN, —NO$_2$, =O, =CH$_2$, trihalomethyl, carbamoyl, aryl$C_{0-10}$alkyl, heteroaryl$C_{0-10}$alkyl, $C_{1-10}$alkyloxy, aryl$C_{0-10}$alkyloxy, $C_{1-10}$alkylthio, aryl$C_{0-10}$alkylthio, $C_{1-10}$alkylamino, aryl$C_{0-10}$alkylamino, N-aryl-N-$C_{0-10}$alkylamino, $C_{1-10}$alkylcarbonyl, aryl$C_{0-10}$alkylcarbonyl, $C_{1-10}$alkylcarboxy, aryl$C_{0-10}$alkylcarboxy, $C_{1-10}$alkylcarbonylamino, aryl$C_{0-10}$alkylcarbonylamino, tetrahydrofuryl, morpholinyl, piperazinyl, hydroxypyronyl, —$C_{0-10}$alkylCOOR$_a$ and —$C_{0-10}$alkylCONR$_b$R$_c$, wherein R$_a$, R$_b$ and R$_c$ are independently selected from hydrogen, alkyl, aryl, or R$_b$ and R$_c$ are taken together with the nitrogen to which they are attached forming a saturated cyclic or unsaturated cyclic system containing 3 to 8 carbon atoms, with at least one substituent.

As used herein, the term "aryl" refers to an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group consisting of halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_a$, and —$C_{0-10}$alkylCONR$_b$R$_c$, wherein R$_a$, R$_b$ and R$_c$ are independently selected from hydrogen, alkyl, aryl or R$_b$ and R$_c$ are taken together with the nitrogen to which they are attached forming a saturated cyclic or unsaturated cyclic system containing 3 to 8 carbon atoms with at least one substituent.

As used herein, the definition of "aryl" includes, but is not limited to, such specific groups as phenyl, biphenyl, naphthyl, dihydronaphthyl, tetrahydronaphthyl, indenyl, indanyl, azulenyl, anthryl, phenanthryl, fluorenyl, pyrenyl and the like.

As used herein, the terms "heteroaryl", "heterocycle" or "heterocyclic" refer to a monovalent unsaturated group having a single ring or multiple condensed (also known as "fused") rings, from 1 to 8 carbon atoms and from I to 4 hetero atoms selected from nitrogen, sulfur or oxygen within the ring. The heteroaryl groups in this disclosure can be optionally substituted with 1 to 3 substituents selected from the group consisting of: halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N—$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_a$, and —$C_{0-10}$alkylCONR$_b$R$_c$ wherein R$_a$, R$_b$ and R$_c$ are independently selected from hydrogen, alkyl, aryl, or R$_b$ and R$_c$ are taken together with the nitrogen to which they are attached forming a saturated cyclic or unsaturated cyclic system containing 3 to 8 carbon atoms with at least one substituent.

As used herein, the definition of "heteroaryl" includes, but is not limited to, such specific groups as thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5]tetrazinanyl-3,6-dione, dihydro-pyrimidinyl-2,4-dione, pyrimidinyl-2,4,6-trione and the like.

As used herein, the term "indazole" refers to a bicyclic heteroaryl having the formula

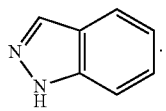

As used herein, the terms "halogen", "halide" or "halo" refer to fluorine, chlorine, bromine, and iodine.

As used herein, the terms "peptide" and "polypeptide" refer to molecular chains formed by a plurality of amino acids which are formed by condensation of the amino group of one acid with the carboxyl group of another.

As used herein, the term a "derivative" in connection with a peptide moiety refers to a form of the peptide in which one or more reaction groups of the compound have been derivatized with a substituent group.

As used herein, the term "an analog" in connection with a peptide moiety refers to a compound which retains chemical structures necessary for functional activity, yet which also contains certain chemical structures which differ from the parent peptide.

As used herein, the term "kinase" refers to any enzyme that catalyzes the addition of phosphate groups to a protein residue; for example, serine and threonine kinases catalyze the addition of phosphate groups to serine and threonine residues.

As used herein, the term "JNK kinase" refers to JNK, also known as C-Jun N-terminal kinase, which is a kinase that binds and phosphophorylates c-Jun on Ser63 and Ser73 within its transcriptional activation domain, and is amitogen-activated protein kinase which is responsive to stress stimuli, such as cytokines ultraviolet irradiation, heat shock, and osmotic shock, and is involved in T cell differentiation and apoptosis.

As used herein, the term "mimetic" in connection with a compound refers to a compound in which chemical structures of the compound necessary for functional activity have been replaced with other chemical structures which mimic the conformation of the compound or peptides thereof.

As used herein, the terms "sample" and "biological sample" refer to any sample suitable for the methods provided by the present disclosure. In one embodiment, the biological sample of the present disclosure is a tissue sample, e.g., a biopsy specimen such as samples from needle biopsy. In other embodiments, the biological sample of the present disclosure is a sample of bodily fluid, e.g., serum, plasma, urine, and ejaculate.

As used herein, the term "effective amount" of a compound refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount," yet, a suitable effective amount may be determined by one of ordinary skill in the art.

As used herein, the term "pharmaceutically acceptable" refers to a compound, additive or composition that is not biologically or otherwise undesirable. For example, the additive or composition may be administered to a subject along with a compound of the disclosure without causing any undesirable biological effects or interacting in an undesirable manner with any of the other components of the pharmaceutical composition in which it is contained.

As used herein, the term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris(hydroxymethyl)aminomethane salt and the like. Additional pharmaceutically acceptable salts are known to those of skill in the art.

As used herein, the term "patient" refers to organisms to be treated by the methods of the present disclosure. Such organisms include, but are not limited to, humans. In the context of the disclosure, the term "subject" generally refers to an individual who will receive or who has received treatment for the treatment of a disease, disorder or pathology.

As used herein, the term "cancer" as used herein, includes any malignant tumor including, but not limited to, carcinoma, sarcoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof.

As used herein, the term "cancerous cell" as used herein, includes a cell afflicted by any one of the cancerous conditions provided herein. Thus, the methods of the present disclosure include treatment of benign overgrowth of melanocytes, glia, prostate hyperplasia, and polycystic kidney disease. The term "carcinoma" refers to a malignant new growth made up of epithelial cells tending to infiltrate surrounding tissues, and to give rise to metastases.

As used herein, the term "ameliorating" or "treating" means that the clinical signs and/or the symptoms associated with the disease, such as cancer, are lessened as a result of the actions performed.

Design, Synthesis and Characterization of Potent and Selective Dual ATP- and Substrate-Competitive Sub-nanomolar Bi-dentate JNK Inhibitors The design and synthesis of potent and selective kinase inhibitors is at the center of considerable efforts from both the pharmaceutical sector and academic research. These efforts are devoted to the design of potent inhibitors targeting the highly conserved ATP binding pocket of kinases. Protein and small molecule kinases also possess binding pockets for substrates and scaffolding proteins that could be equally used to design specific inhibitors. However, these binding surfaces are usually large and shallow hence not particularly suitable for the design of small drug like inhibitors with sufficient potency. It has been found that bidentate compounds, which link the binding energies of weakly interacting ATP and substrate mimetics, result in potent and selective inhibitors. For example, the bi-dentate compounds of formula (I), were designed against the protein kinase JNK. In view of its favorable inhibition profile, selectivity, and ability to function in the cellular milieu and in vivo, these compounds represents a dual ATP- and substrate-competitive kinase inhibitors.

The c-Jun N-terminal kinases (JNKs) are a series of serine/threonine protein kinases belonging to the mitogen activated protein kinase (MAPK) family. Three distinct genes encoding JNKs have been identified, JNK1, JNK2, and JNK3, and at least 10 different isoforms exist in mammalian cells[1-3]. JNK1, JNK2, and JNK3 share more than 90% amino acid sequence identity and the ATP pocket is >98% homologous. JNK1 and JNK2 are ubiquitously expressed, whereas JNK3 is most commonly found in the brain, cardiac muscle, and testis. JNK activation in response to stimuli such as stress or cytokines results in activation of several transcription factors and cellular substrates implicated in inflammation, insulin signaling, mRNA stabilization, and cell proliferation and survival[3-6]. Because of the link between these pathways and the pathogenesis of diseases such as Parkinson's and Alzheimer's and inflammatory diseases, cancer, diabetes, atherosclerosis, and stroke, JNK inhibitors are expected to be useful therapeutic agents[1,3,7,8].

JNK binds to substrates and scaffold proteins, such as JIP-1, that contain a D-domain, as defined by the consensus sequence $R/K_{(2-3)}X_{(1-6)}L/I-X-L/I$. A JIP1 D-domain peptide corresponding to amino acids 153-164 (pepJIP1; sequence RPKRPTTLNLF (SEQ ID NO:16); MW 1343) inhibits JNK activity in vitro and in cell while displaying extraordinary selectivity with negligible inhibition of the closely related MAP kinases p38 and Erk. The mechanism of this inhibition is thought to be due to competition of pepJIP1 with the D-domains of JNK substrates or upstream kinases. In order to increase stability and increase cell permeability of pepJIP1 an all-D retro-inverso amino acid pepJIP1 fused to the cell permeable HIV-TAT peptide (D-JNKI) was devised (sequence Ac-tdqsrpvqpflnlttprrprppprrrqrrkkrg-CONH$_2$(SEQ ID NO:17); MW =3395). D-JNKI significantly decreases c-Jun phosphorylation by JNK when tested in cell, however, albeit very selective, inhibition studies suggest that D-JNKI is only a modest JNK inhibitor. In comparison, the small molecule ATP mimetic SP600125 is very potent in vitro but not very selective for JNK. Hence, most of the current efforts focus on optimization of SP600125 and other ATP mimetics for the design of JNK inhbitors.

Using a combination of structure-based design guided by the X-ray structure of JNK1 in complex with pepJIP1 and SP600125, as well as NMR fragment-based drug discovery approaches[20], it has been found that by using linking molecules that span these two sites, it has unexpectedly been found to generate selective, high affinity bi-dentate JNK modulators. Indeed, provided herein are bi-dentate molecules with the aforementioned characteristics that functions as a JNK inhibitor both in vitro and in cell as well as exhibiting in vivo efficacy in a type 2 diabetes model.

Figure 4:
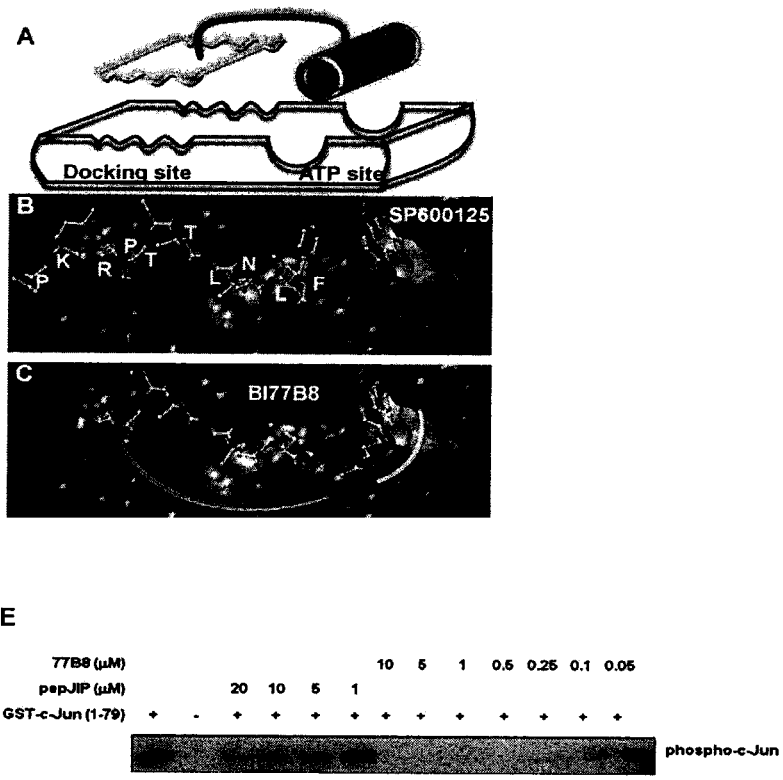
FIG. 4 provides the fragment-based design and synthesis of bi-dentate JNK inhibitors: A) Schematic representation of the proposed approach overlaid on the surface representation of JNK1 in complex with pepJIP1 (RPKRPTTLNLF) (SEQ ID NO:1) and the ATP mimic SP600125(PDB-ID 1UKI). The surface generated with MOLCAD and color coded according to cavity depth (blue, shallow; yellow, deep); B) Docked structure of pepJIP1 and SP600125 on the surface of JNK1; C) Docked structure of the bi-dentate compound BI77B8 on the surface of JNK1. D) Scheme for the synthesis of BI77B1and the bi-dentate BI77B8 (see methods for experimental details). E) In vitro JNK kinase activity inhibition by BI77B8.

In the realm of drug discovery, fragment-based drug design (FBDD) approaches are becoming increasingly successful in tackling challenging targets, such as those involving protein-protein interactions[21]. A common FBDD approach consists of designing bi-dentate compounds chemically linking two weakly interacting scaffolds that occupy adjacent pockets on the target's surface (FIG. 4). In this case, the free energy of binding of the resulting bi-dentate compound with respect to those of the individual fragments can be expressed as:

$$\Delta G^{AB} = \Delta H^A + \Delta H^B - T\Delta S^{AB} = -RT \ln(K_D^A * K_D^B * E)$$

where, R represents the Boltzman constant, T is the temperature of the system, $\Delta H^A$ and $\Delta H^B$ are the enthalpy of binding of fragments A and B respectively, $\Delta S^{AB}$ represents the entropy loss upon binding of the bi-dentate compound, and $K_D^A$ and $K_D^B$ are the dissociation constants of the individual initial binders and E is the linking coefficient[22]. The recently determined X-ray structure of JNK1 in complex with pepJIP1 and the ATP-mimic SP600125[23], reveals a close proximity between the ATP and the docking binding sites, suggesting the possibility of obtaining high affinity and selective compounds by designing appropriate bi-dentate molecules. It is surprisingly been found that by tailoring a weak docking site binder to a weakly interacting ATP-mimic, provides potent and selective inhibitors of JNK and, potentially, this approach could be applied to several other proteins and small molecule kinases.

In order to define an optimal interacting docking peptide sequence for JNK, twenty peptide sequences were tested, which were derived from its putative substrates and scaffolding proteins, all presenting a D-domain consensus motif. Each peptide was tested for its ability to displace pepJIP1 (residues 153-164) from JNK1 by using a Dissociation Enhanced Lanthanide Fluoro-Immuno Assay (DELFIA) platform. DELFIA is a heterogeneous assay whereby a biotin-linked pepJIP1 is adsorbed onto a streptavidin-coated plate followed by incubation with GST-JNK1. Detection of the pepJIP1/GST-JNK1 complex is facilitated by a highly fluorescent anti-GST Eu-antibody conjugate (Perkin-Elmer). Based on these data, a minimal peptide sequence "RPTTLNL" (SEQ ID NO:4) was identified as necessary and sufficient to displace full-length pepJIP1 in this assay.

The design of a weak ATP mimetic JNK inhibitor was based on the structure of SP600125 (FIG. 4)[23]. Given that SP600125 was found to potently inhibit several protein kinases[16,17,19], in order to increase JNK selectivity and also facilitate subsequent synthetic efforts, the keto group from SP600125 was removed. Furthermore, based on its docking mode, a convenient position to elongate the ATP-mimetic towards the docking site was identified, by using a combination of structure-based design guided by NMR-relaxation measurements using paramagnetic spin-labeling approaches[20]. These efforts resulted in the design of BI77B1 (FIG. 4). The synthesis of BI77B1 starts from the iodination of 1-azaindole with iodide and its protection with trimethylsilylethoxy methyl chloride, followed by a Suzuki coupling between 3 and 4-methoxycarbonylphenylboronic acid and attachment of the designed 3-carbon linker (FIG. 4).

BI77B1 is a relatively weak ATP mimetic, inhibiting JNK1 phosphorylation of the substrate ATF2 in a Time-Resolved Fluorescence Resonance Energy Transfer (TR-FRET) based LanthaScreen™ kinase activity assay (Invitrogen, Carlsbad, Calif.) with 14 µM IC$_{50}$ value. Similarly, the minimal peptide sequence RPTTLNL was unable to inhibit JNK1 phosphorylation of the substrate ATF2 in a Time-Resolved Fluorescence Resonance Energy Transfer (TR-FRET) based LanthaScreen™ kinase activity assay (Invitrogen, Carlsbad, Calif.) at concentrations up to 25 µM, hence representing a fairly weakly interacting substrate binding scaffold. However, when linked to the indazole moiety of BI77B1, the resulting compound (BI77B8; FIG. 4) is able to compete with pepJIP1 for JNK1 binding and inhibit JNK1 kinase activity with remarkable sub-nanomolar affinities (Table 3).

TABLE 3

In vitro activity data for reported JNK inhibitors.

| Molecule (MW) | ID (MW) | pepJIP Displacement | Kinase Inhibition |
|---|---|---|---|
| 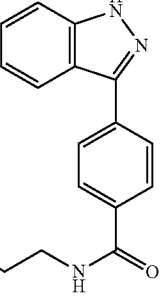 | BI-77B1 (294) | $IC_{50} = >50\ \mu M$ | $IC_{50} = 14\ \mu M$ |
| Ac-RPTTLNL-OH (SEQ ID NO: 4) | BI-77F10 (856) | $IC_{50} = 4.5\ \mu M$ | $IC_{50} = >50\ \mu M$ |
| 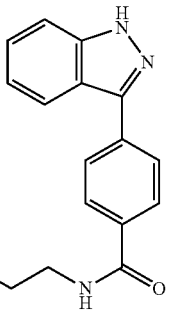 | BI-77B8 (1236) | $IC_{50} = 0.9\ \mu M$ | $IC_{50} = 0.7\ \mu M$ |
| Ac-tdqsrpvqpflnlttprrprpprrrqrrkkrg-OH (SEQ ID NO: 17) | D-JNKI (3994) | $IC_{50} = \sim 10\ \mu M$ | $IC_{50} = >50\ \mu M$ |
| 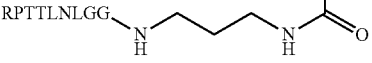<br>(SEQ ID NO: 6) | BI-87G9 (2728) | $IC_{50} = 46$ nM<br>$Ki = 1.5$ nM | $IC_{50} = 18$ nM<br>$Ki = 2$ nM |

Figure 4D:
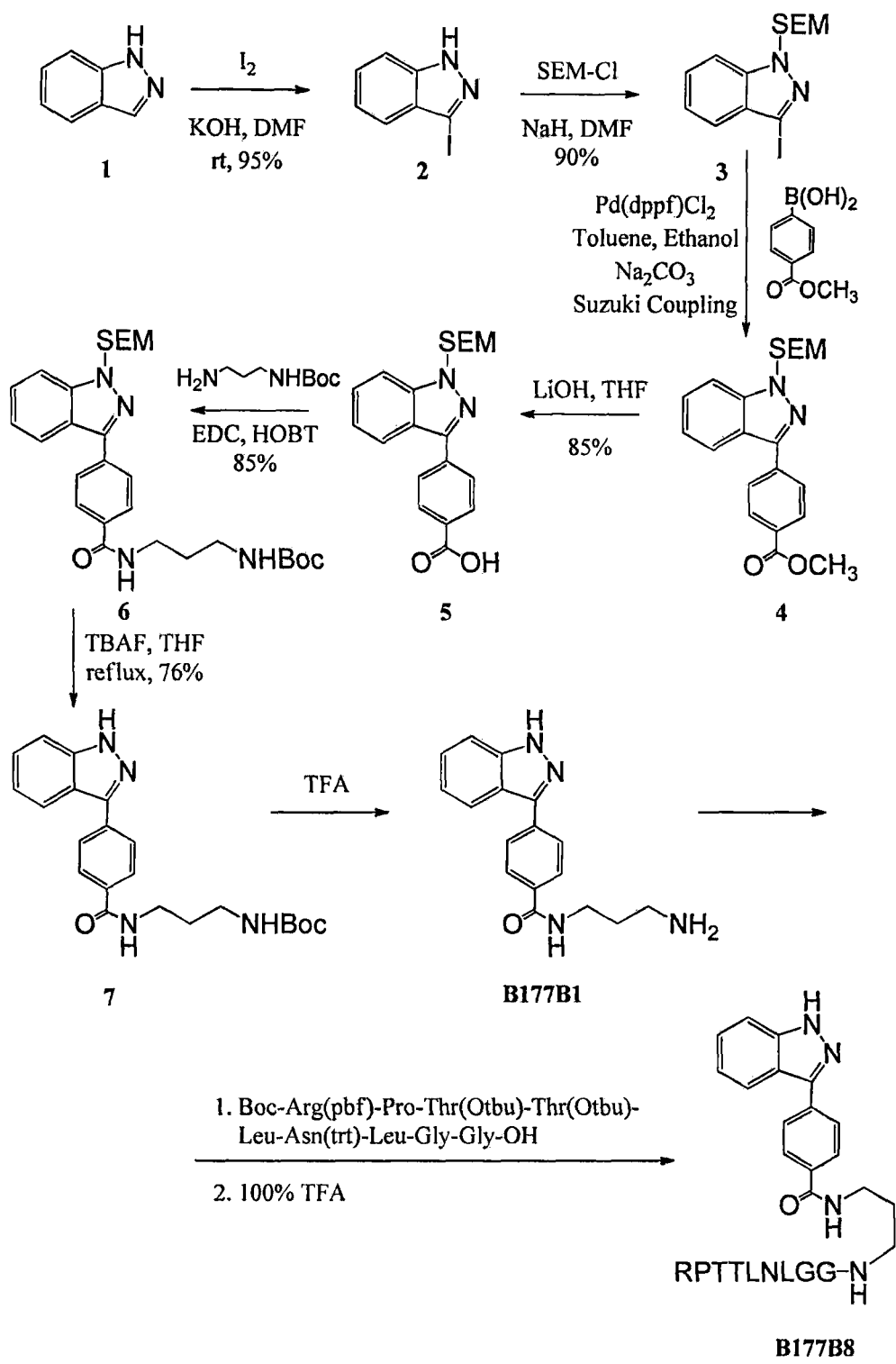

BI77B1 is a relatively weak ATP mimetic, inhibiting JNK1 phosphorylation of the substrate ATF2 in a Time-Resolved Fluorescence Resonance Energy Transfer (TR-FRET) based LanthaScreen™ kinase Direct comparison of kinase inhibition properties of BI77B8 (MW 294) with pepJIP1 (MW 1343) clearly demonstrated an improvement of over 100-fold (FIG. 4D). Hence, by linking the binding energy of a minimal pepJIP1 sequence with a modest SP600125 derived ATP mimetic we successfully produced a very potent bi-dentate molecule representing a new class of JNK inhibitors.

Figure 5:
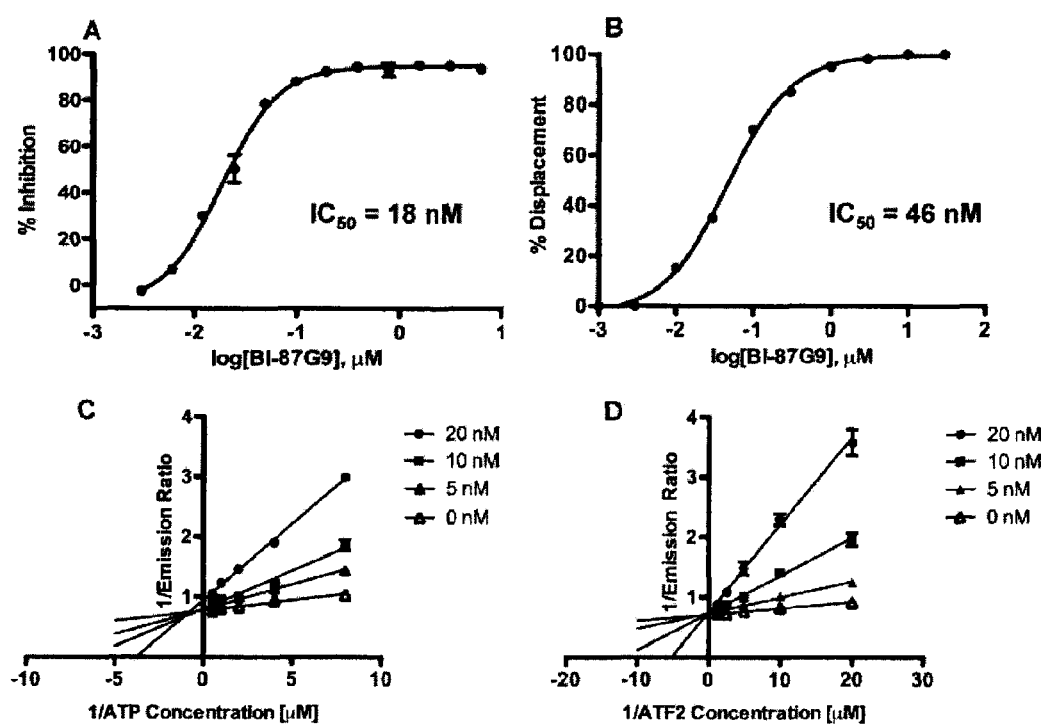
FIG. 5 provides the in vitro characterization of BI87G9. A) Dose dependent displacement of biotinylated pepJIP1 from GST-JNK1 and B) JNK kinase activity inhibition by BI87G9. C) and D) Lineweaver-Burk analysis with compound BI87G9.

In order to confer further favorable pharmacological properties to this compound for in vivo studies, analogous to the clinical candidate D-JNK1[15], an all-D retro-inverso version of BI77B8 fused to the cell penetrating HIV-TAT sequence was prepared. The resulting compound, BI87G9 (Table 3), efficiently competes with pepJIP1 for binding to JNK1 as well as strongly inhibits JNK1 kinase activity (FIGS. 5A and 5B), with respective $IC_{50}$ values of 18 and 46 nM respectively. Using the same in vitro LanthaScreen™ kinase activity assay and the same ATF2 substrate, BI87G9 was found to be inactive versus p38α at concentrations up to 100 μM, a member of the MAPK family with highest structural similarity to JNK thus demonstrating its selectivity. Lineweaver-Burk analysis indicates that BI87G9 is competitive with both ATP and ATF2 for binding to JNK1 with apparent K(i) values of 2 and 1.5 nM respectively (FIGS. 5C and 5D).

Figure 6:
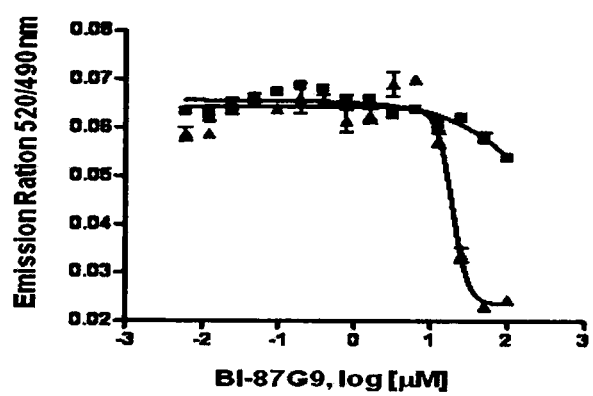
FIG. 6 provides the bio-evaluation of BI87G9. A) TR-FRET analysis of c-Jun phosphorylation upon TNF-α stimulation of B16-F10 cells in the presence of increasing BI87G9 (closed triangles) and D-JNK1 (closed squares). It should be noted that the cell-based system employed makes use of a GFP-c-Jun stable expression system. As a result, the levels of GFP-c-Jun in these cells are higher than endogenous levels. This could have an inflationary effect on the $EC_{50}$ values obtained with this assay when testing substrate competitive compounds. B) BI87G9 and D-JNK1 effect on TNF-α and IL-1β levels after 5 hours of exposure to LPS as compared to vehicle control. Results shown as percent of vehicle control±S.D. (n=3). Cytokine production was measured directly from cell culture medium by a sandwich immunoassay (Meso Scale Discovery). C) Effect of BI87G9 and D-JNK1 (25 mg/kg) on glucose tolerance in 26-week-old NONcNZO10/LtJ mice from Harlan (Jackson Labs, Bar Harbor, Me. 04609 USA). Closed diamonds, vehicle control; closed squares, 25 mg/kg BI87G9; closed triangle, 25 mg/kg D-JNK1.
Figure 6:
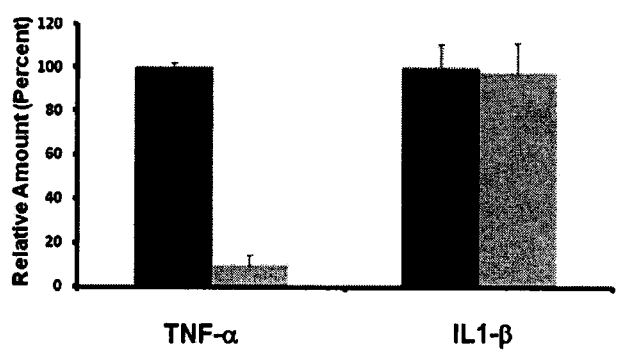
Figure 6:
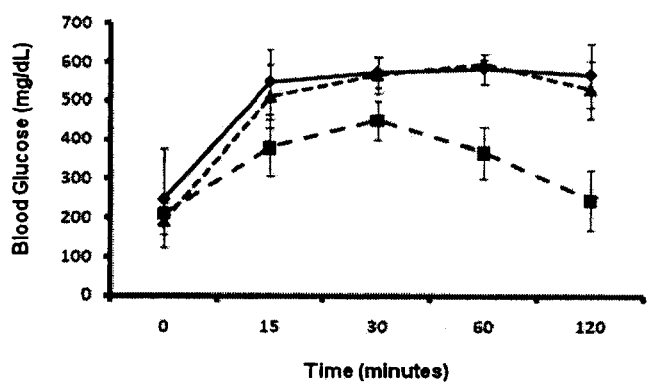

In an attempt to further profile the biological properties of BI87G9, its ability to function in the context of a complex cellular milieu with that of D-JNK1 was compared. For this analysis, a cell-based LanthaScreen™ kinase assay[24] was used. In this assay, BI87G9 is significantly more effective at inhibiting tumor necrosis factor-α (TNF-α) stimulated phosphorylation of c-Jun in B16-F10 melanoma cells ($EC_{50}=14$ μM; FIG. 6A). To further profile BI87G9 efficacy in cells as well as demonstrate its selectivity, the ability of BI87G9 to inhibit the release of cytokines from RAW 264.7 mouse macrophage cells in response to lipopolysaccharide (LPS) was tested. LPS stimulated secretion of TNF-α from macrophages is dependent on JNK activation[25] whereas IL-1β secretion from RAW 264.7 cells is known to be p38 dependent[26]. It was found that BI87G9 is able to inhibit JNK dependant TNF-α release while p38α dependant IL-1β secretion was unaffected (FIG. 6B). Taken together, these findings establish that BI-87G9 is a first class of potent and selective dual substrate and ATP competitive JNK bi-dentate inhibitor able to function efficiently and selectively in a cellular context.

JNK activation has been linked to the impaired glucose tolerance associated with type 2 diabetes[7,27]. Therefore, the ability of BI87G9 to restore glucose tolerance in the type 2 diabetes mouse model NONcNZO10/LtJ[28] (Jackson Labs, Bar Harbor, Me. 04609 USA) was tested. For this analysis, glucose intolerant NONcNZO10/LtJ mice were injected daily for four days with 25 mg/kg BI87G9. The ability of mice to process glucose injected intraperitoneally was then measured. BI87G9 was remarkably effective in restoring normoglycemia without inducing hypoglycemia compared to both the vehicle control and D-JNK1 (FIG. 6C). Thus, the ability of BI87G9 to improve glucose tolerance is consistent with its proposed function as an effective JNK inhibitor.

By applying the principles of fragment-based drug discovery to the design of dual ATP- and substrate-competitive kinase inhibitors, a first class of bi-dentate molecules with superior JNK inhibitory properties has been developed. This approach may find wide applications in the design and synthesis of other potent and selective bi-dentate kinase inhibitors. Regarding the reported bi-dentate compounds, given that D-JNK1 is currently a clinical candidate (under XG102 by Xigen Corp., Lausanne, CH), BI87G9, having markedly improved biochemical and pharmacological properties and even reduced molecular weight over D-JNK1, could equally well enter further clinical investigations.

According to embodiments of the present disclosure, there are provided compounds having the general structure A or pharmaceutically acceptable salts thereof:

Het-L-P     (A)

wherein Het is an aromatic moiety comprising a heterocyclic structure, P is a peptide moiety comprising a peptide or a polypeptide, and L is a linking moiety, wherein L links the aromatic moiety to the peptide moiety.

In some embodiments, the aromatic moiety Het comprises a derivative of indazole including the following moiety:

wherein R is an aromatic substituent, e.g., an unsubstituted or substituted phenylene group, and $R_1$ is hydrogen or a substituent selected from the group consisting of a straight-chained alkyl, a branched alkyl, and a halogen, and wherein the moiety Het is connected to the linking moiety via the aromatic substituent R.

In some embodiments of the disclosure, in compounds of the general structure A, the linking moiety L is a di-amide structure, i.e., the linking moiety L comprises two terminal amido groups connected by a hydrocarbon bridge and has the following structure,

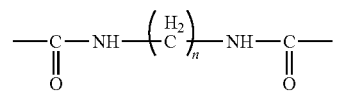

wherein the bridge can include between two and eight consecutively positioned methylene groups. In other embodiments, examples of a linking moiety L that can be used include the structures $-(CH_2)_n-$, $-O-(CH_2)_n-O-$, $-(CH_2)-$phenylene-, $-NHSO_2-(CH_2)_n-CONH-$, and $-CONH-(CH_2)_n-CONH-$, wherein n is an integer having the value between 2 and 8.

Compounds having the general structure A shown above include a peptide moiety P. When the compound is brought in contact with a kinase, the peptide moiety P can bind to the kinase docking site. Those having ordinary skill in the art can determine what particular peptides could be used in compound A. Typical non-limiting examples of some specific peptides that can be so used include $Xaa_{(0-8)}LNLGGXaa_{(0-8)}$ (SEQ ID NO:8), $Xaa_{(0-8)}LNLXaa_{(0-8)}$ (SEQ ID NO:9), an L optical isomer of any of RPTTLNLGG (SEQ ID NO:1), PTTLNLGG (SEQ ID NO:2), LNLGG (SEQ ID NO:3), RPTTLNL (SEQ ID NO:4), PTTLNL (SEQ ID NO:10), or LNL (which can be optionally N-myristoilated, if desired) or small molecule mimetics thereof, a D optical isomer of any of GGLNLTTPR (SEQ ID NO:11), GGLNLTTP (SEQ ID NO:12), GGLNL (SEQ ID NO:13), LNLTTPR (SEQ ID NO:14), LNLTTP (SEQ ID NO:15), or LNL (which can be optionally C-myristoilated, if desired), or small molecule mimetics thereof. The peptide moiety may contain one or more amino acid derivatives, analogs, mimetics, or non-natural amino acids.

Examples of peptide derivatives include peptides in which an amino acid side chain, the peptide backbone, or the amino- or carboxy-terminus has been derivatized. An example of an analog of a naturally occurring peptide is a peptide which includes one or more non-naturally-occurring amino acids.

Examples of some specific compounds that are within the purview of the present disclosure and are described by the general structure A include compounds I-VIII:

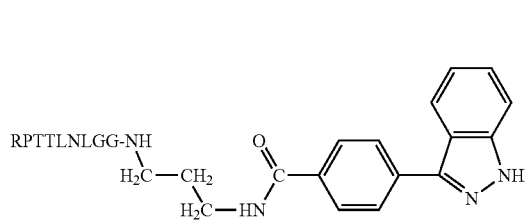

Compound I comprising SEQ ID NO: 1

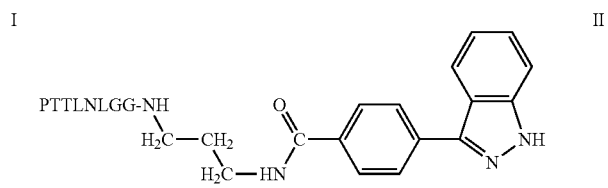

Compound II comprising SEQ ID NO: 2

-continued
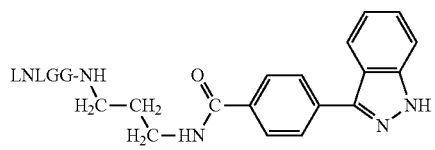
Compound III comprising SEQ ID NO: 3
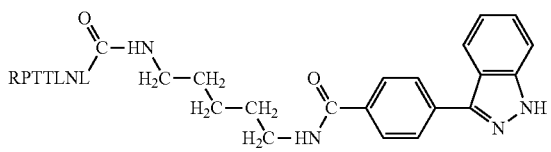
Compound IV comprising SEQ ID NO: 4
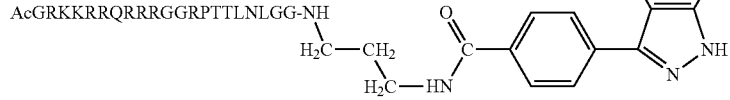
Compound V comprising SEQ ID NO: 5
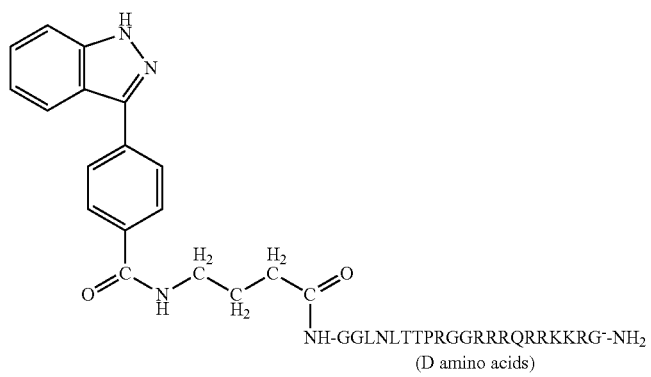
(D amino acids)
Compound VI comprising SEQ ID NO: 6
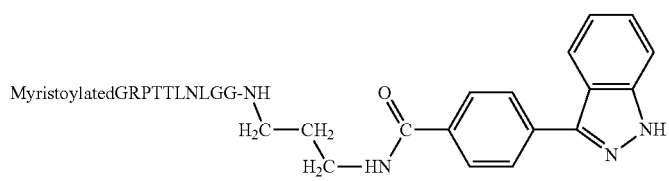
Compound VII comprising SEQ ID NO: 7
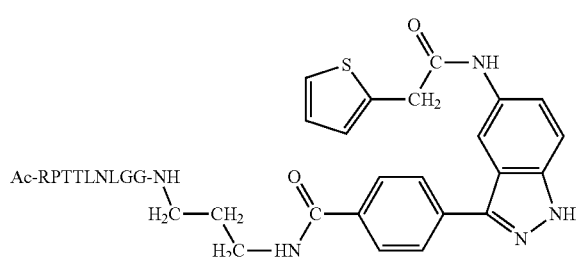
Compound VIII comprising SEQ ID NO: 1

As can be seen from the above formulae, each of the compounds I-VIII is an adduct which is a product of conjugation of a benzamide to the respective peptide, i.e., to the peptide RPTTLNLGG (SEQ ID NO:1), PTTLNLGG (SEQ ID NO:2), LNLGG (SEQ ID NO:3), or RPTTLNL (SEQ ID NO:4); for example, for compounds I-III, the benzamide is N-(aminopropyl)-4-(1H-indazol-3-yl) benzamide.

According to other embodiments of the present disclosure, a compound of formula I is provided:

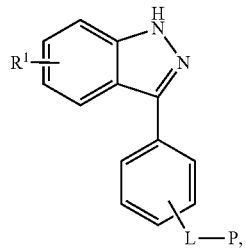

(I)

or a pharmaceutically acceptable salt thereof, wherein:

$R^1$ is hydrogen, straight-chained alkyl, branched alkyl, halogen, nitro, or $NHC(O)CH_2C_4H_3S$;

L is a linking moiety selected from the group consisting of (a) —CONH—$(CH_2)_n$—NH—, (b) —CONH—$(CH_2)_n$—NHCO—, (c) —CONH—$(CH_2)_n$—CONH—, (d)—$(CH_2)_n$—, (e) —O—$(CH_2)_n$—O—, (f) —$(CH_2)$-phenylene-, and (h) —$NHSO_2$—$(CH_2)_n$CONH—, wherein n is an integer between 2 and 8; and P is a peptide consisting of the sequence selected from the group consisting of RPTTLNL (SEQ ID NO:4), N-myristoilated RPTTLNL (SEQ ID NO:4), and GGLNLTTPRGGR-RRQRRKKRG (SEQ ID NO:6).

According to other embodiments of the present disclosure, a compound of formula I is provided, wherein the compound binds to a JNK kinase docking site.

According to other embodiments of the present disclosure, a compound of formula I is provided, wherein L is —CONH—$(CH_2)_n$—NH—; and P is a peptide consisting of the sequence selected from RPTTLNL (SEQ ID NO:4), and GGLNLTTPRGGRRRQRRKKRG (SEQ ID NO:6).

According to other embodiments of the present disclosure, a compound of formula I is provided, wherein $R^1$ is hydrogen or straight chain alkyl; and L is —CONH—$(CH_2)_3$—NH—.

According to other embodiments of the present disclosure, a compound of formula I is provided, wherein the compound of formula I has formula II:

(SEQ ID NO: 11)

(II)

or wherein the compound of formula I has formula III:

(SEQ ID NO: 6 (D amino acids))

(III)

According to other embodiments of the present disclosure, pharmaceutical compositions are provided, including the compound of formula I or the compound of formula II or formula III, and a pharmaceutically acceptable carrier.

According to other embodiments of the present disclosure, pharmaceutical compositions are provided, including the compound of formula I or the compound of formula II or formula III, and a pharmaceutically acceptable carrier, further including an additional compound selected from the group consisting of: (1) an estrogen receptor modulator, (2) an androgen receptor modulator, (3) retinoid receptor modulator, (4) a cytotoxic agent, (5) an antiproliferative agent, (6) a prenyl-protein transferase inhibitor, (7) an HMG-CoA reductase inhibitor, (8) an HIV protease inhibitor, (9) a reverse transcriptase inhibitor, (10) another angiogenesis inhibitor, and (11) a PPAR-gamma agonist.

According to other embodiments of the present disclosure, methods for treating retina vascularization are provided, including administering to a subject a therapeutically effective amount of a pharmaceutical composition of the compound of formula I, formula II or formula III.

According to other embodiments of the present disclosure, methods for treating diabetic retinopathy are provided, including administering to a subject a therapeutically effective amount of a pharmaceutical composition of the compound of formula I, formula II or formula III.

According to other embodiments of the present disclosure, kits are provided, including a packaging material and a pharmaceutical composition of formula I, formula II or formula III contained within the packaging material, wherein the packaging material includes a label, which indicates that the composition can be used for treating a disorder, disease, or pathology in a subject in need thereof.

In another aspect of the disclosure, the subject compounds can be used as part of a treatment regimen for cancer. In some cases, the treatment of cancer may include the treatment of solid tumors or the treatment of metastasis. Metastasis is a form of cancer wherein the transformed or malignant cells are traveling and spreading the cancer from one site to another. Such cancers include cancers of the skin, breast, brain, cervix, testes, etc. More particularly, cancers may include, but are not limited to the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), neuroblastoma, pheochromocytoma, paraganlioma, meningioma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia. Skin cancer includes malignant melanoma, basal cell carcinoma, squamous cell carcinoma, Karposi's sarcoma, moles dysplastic nevi, lipoma, angioma, dermatofibroma, keloids, and psoriasis. Thus, exemplary cancers that can be treated with the compounds of the disclosure include, but are not limited to, cancers of the brain, genitourinary tract, lymphatic system, stomach, larynx and lung.

In another aspect, the compounds are useful in the treatment of diseases where suppression, attenuation of the activity, and/or inhibiting kinases, for example, such kinases as JNK, p38, ERK, SRC, or JAK may be desirable. These include, but are not limited to, diabetes (both type I and type II), cerebral ischemia and stroke, neuropathic pain, neurological disorders and neurodegeneration, hepatic injury, treatment of viral infections, lung ischemia/reperfusion damage, acoustic trauma, macular degeneration, retinal vascularization, diabetic retinopathy, cancer, and inflammation. Moreover, the compounds described in the disclosure may be useful in clinical transplantation of pancreatic islet b-cells.

As such, the disclosure provides methods of treating cancer in a subject. Such methods include administering to an individual or a cell, a therapeutically effective amount of a compound of the disclosure. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. However, the method can also be practiced in other species, such as avian species (e.g., chickens).

In another aspect, the present disclosure provides a method of ameliorating or treating a tumor in a subject with the compounds of the disclosure. The signs or symptoms to be monitored will be characteristic of a particular cancer or melanoma and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

Accordingly, the methods of the disclosure are useful for providing a means for practicing personalized medicine, wherein treatment is tailored to a subject based on the particular characteristics of the cancer cells in the subject. In one embodiment, the method can be practiced by contacting a sample of cells from the subject with at least one compound of the disclosure, and measuring the ability of the compound to displace the binding between JNK and the L-JIP peptide. In another embodiment, the method can be practiced by contacting a sample of cells from the subject with at least one compound of the disclosure, and measuring the ability of the compound to inhibit JNK-mediated phosphorylation of substrates. In yet another embodiment, the method can further include testing the compound against a related kinase, e.g., p38 to demonstrate selectivity and identify the compound as useful for treating the cancer.

The sample of cells examined according to the present method can be obtained from the subject to be treated, or can be cells of an established cancer cell line of the same type as that of the subject. In one aspect, the established cancer cell line can be one of a panel of such cell lines, wherein the panel can include different cell lines of the same type of cancer and/or different cell lines of different cancers. Such a panel of cell lines can be useful, for example, to practice the present method when only a small number of cancer cells can be obtained from the subject to be treated, thus providing a surrogate sample of the subject's cancer, and also can be useful to include as control samples in practicing the present methods.

Preferred cell types for use in the disclosure include, but are not limited to, mammalian cells, including animal (rodents, including mice, rats, hamsters and gerbils), primates, and human cells, particularly cancer cells of all types, including breast, skin, lung, cervix, testes, colorectal, leukemia, brain, etc.

Once disease is established and a treatment protocol is initiated, the methods of the disclosure may be repeated on a regular basis to evaluate whether displacement of the binding between JNK and the L-JIP peptide and/or inhibition of JNK-mediated phosphorylation in the subject begins to approximate that which is observed in a normal subject. The results obtained from successive assays may be used to show the efficacy of treatment over a period ranging from several days to months. Accordingly, the disclosure is also directed to methods for monitoring a therapeutic regimen for treating a subject having cancer. A comparison of the level of displacement of the binding between JNK and the L-JIP peptide and/or inhibition of JNK-mediated phosphorylation prior to and during therapy indicates the efficacy of the therapy. Therefore, one skilled in the art will be able to recognize and adjust the therapeutic approach as needed.

Accordingly, the compounds having the structure A, including the specific compounds I-X, or pharmaceutically acceptable salts thereof can be used for preparing pharmaceutical compositions, e.g., by combining these compounds and pharmaceutically acceptable carriers. The pharmaceutical compositions can then be used in pharmacologically effective doses for the treatment of various disorders, diseases, and pathologies, such as cancer, diabetes (including diabetic retinopathy), neurological disorders, diseases in which angiogenesis is implicated (e.g., ocular diseases), and retinal vascularization.

If the pharmaceutical compositions are used for the treatment of cancer, the kinds of cancer that can be so treated include, for example, cancers of the brain, genitourinary tract, lymphatic system (e.g., histiocytic lymphoma), stomach, larynx, lung (e.g., lung adenocarcinoma or small cell lung cancers), pancreatic cancer, glioblastomas, breast cancer (e.g., breast carcinoma), colorectal cancer, and prostate cancer.

Various synthetic schemes can be designed for manufacturing the products having the structure A, including the specific compounds I-X. To exemplify, but not limit, the present disclosure, in one embodiment, the reaction scheme (A) shown below in the "Examples" portion of the application can be employed for making compound I. If desired, other synthetic processes can be designed by those having ordinary skill in the art.

Pharmaceutically acceptable salts of the compounds of the present disclosure may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The above-described compounds, including compounds I-X, can be formulated as pharmaceutical compositions and administered to a mammalian host, such as a human patient in a variety of forms adapted to the chosen route of administration, e.g., orally or parenterally, by intravenous, intraperitoneal, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisnis can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds, including the species I-X can be determined by comparing their in vitro activity, and in vivo activity in animal models. Methods for the extrapolation of effective dosages in mice, and other animals, to humans are known to those having ordinary skill in the art who can, for example, be guided by the procedures described in U.S. Pat. No. 4,938,949.

Generally, the concentration of the compounds, including the species I-X in a liquid composition, such as a lotion, can be between about 0.1 and 25 mass %, such as between about 0.5 and 10 mass %. The concentration in a semi-solid or solid composition such as a gel or a powder can be between about 0.1 and 25 mass %, such as between about 0.5 and 2.5 mass %.

The amount of the compounds, including the species I-X, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose can be in the range of between about 0.5 and 100 mg/kg, e.g., between about 10 and 75 mg/kg of body weight per day, such as between about 15 and 60 mg/kg/day. The compounds, including the species I-X can be conveniently administered in unit dosage form; for example, containing 5 to 1000 mg, such as 10 to 750 mg, for example, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Optionally, the compositions of the present disclosure can be administered to a patient in need thereof in combination with other therapeutically beneficial agent(s). Such additional therapeutically beneficial agent(s) can include an estrogen receptor modulator, an androgen receptor modulator, a retinoid receptor modulator, a cytotoxic agent, an antiproliferative agent, a prenyl-protein transferase inhibitor, an HMG-CoA reductase inhibitor, an HIV protease inhibitor, a reverse transcriptase inhibitor., an angiogenesis inhibitor, or a PPAR-gamma agonist.

If an additional angiogenesis inhibitor is used in combination with the compositions of the present disclosure, examples of specific angiogenesis inhibitors that can be so used include a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-alpha, interleukin-12, pentosan polysulfate, a cyclooxygenase inhibitor, carboxyamidotriazole, combretastatin A-4, squalamine, 6—O—(chloroacetyl-carbonyl)-fumagillol, thalidomide, angiostatin, troponin-1, or an antibody to VEGF.

In addition, optionally, the compositions of the present disclosure can be administered to a patient in need thereof in combination with a steroidal anti-inflammatory compound or with an anti-hypertensive compound.

EXAMPLES

The following examples are intended to further illustrate but not limit the scope of the disclosure.

Example 1

Synthesis of Compound I

Compound I comprising SEQ ID NO:1 shown above was synthesized according to the reaction scheme (A).

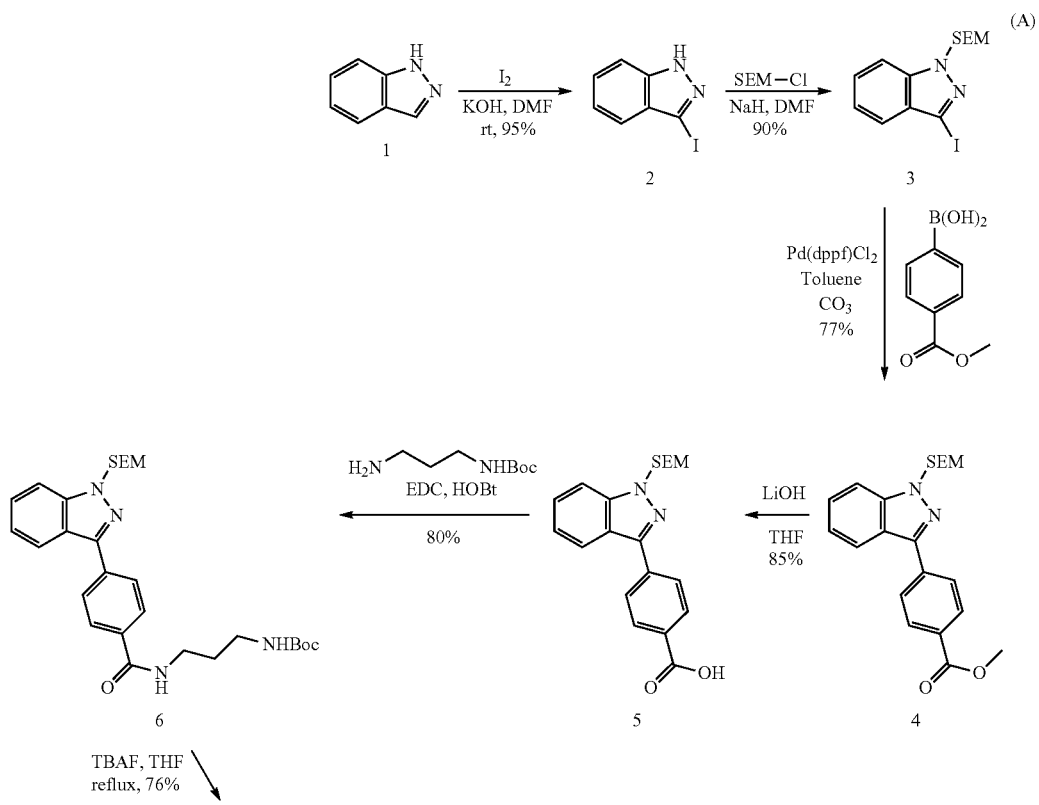

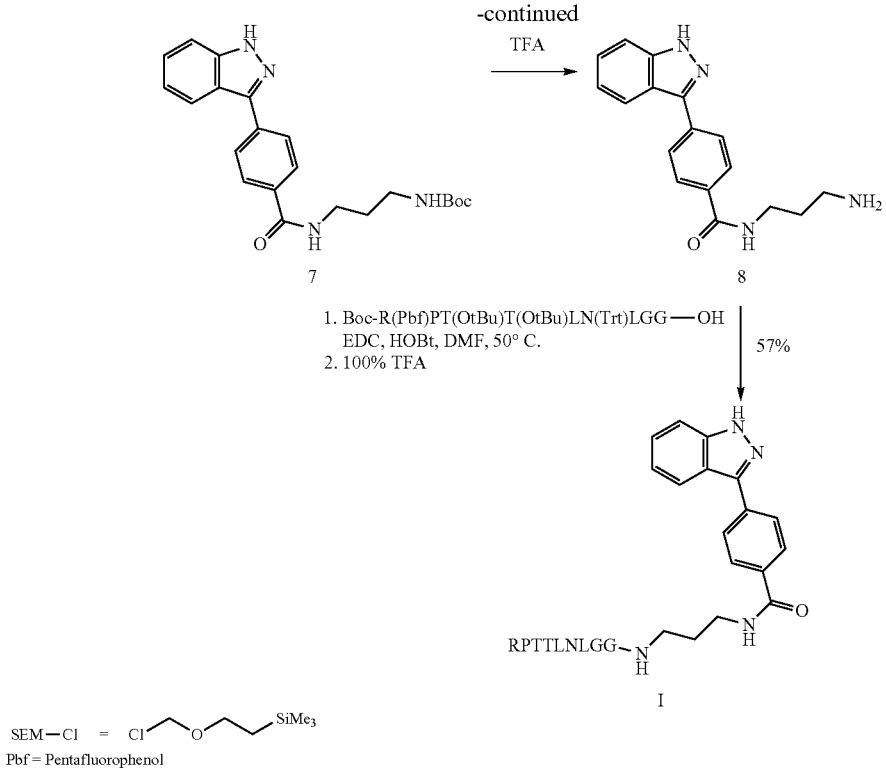

SEM—Cl = Cl–CH2–O–CH2CH2–SiMe3
Pbf = Pentafluorophenol
Trt = Trityl

Example 2
Properties of Compounds of the Disclosure

Compounds of the present disclosure were tested using Delfia Assay and Kinase Assay and the data for $IC_{50}$ were obtained. The results are shown in Tables 1 (both assays) and 2 (Kinase Assay only). The data for various peptides not bonded to any compounds of the present inevntion is provided in Table 1 for comparison purposes.

TABLE 1

Comparative Results on Inhibition Using Compounds

| Compound | Delfia Assay (Displacement of L-JIP1 peptide from JNK) | Kinase Activity Assay (JNK) | Kinase Activity Assay (p38) |
|---|---|---|---|
| Compound I comprising SEQ ID NO: 1 | 0.002 | 0.0007 | 0.19 |

$IC_{50}$, μM

TABLE 1-continued

Comparative Results on Inhibition Using Compounds

| Compound | IC$_{50}$, µM | | |
|---|---|---|---|
| | Delfia Assay (Displacement of L-JIP1 peptide from JNK) | Kinase Activity Assay (JNK) | Kinase Activity Assay (p38) |
| Compound II comprising SEQ ID NO: 2 | 0.08 | 0.15 | ND |
| Compound III comprising SEQ ID NO: 3 | 0.6 | 0.3 | ND |
| Compound V comprising SEQ ID NO: 5 | 0.026 | 0.002 | ND |
| Compound VI comprising SEQ ID NO: 6 | 3.2 | 0.018 | 0% at 50 µM |

TABLE 1-continued

Comparative Results on Inhibition Using Compounds

| Compound | IC$_{50}$, μM | | |
|---|---|---|---|
| | Delfia Assay (Displacement of L-JIP1 peptide from JNK) | Kinase Activity Assay (JNK) | Kinase Activity Assay (p38) |
|  Compound VII comprising SEQ ID NO: 7 | 0.047 | 0.007 | 25% at 50 μM |
| 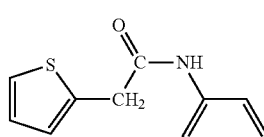 Compound VIII comprising SEQ ID NO: 1 | 0.001 | 0.0003 | 3% at 50 μM |
| 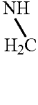 Product 8 on Scheme (A) | ND*) | 14 | ND |
| 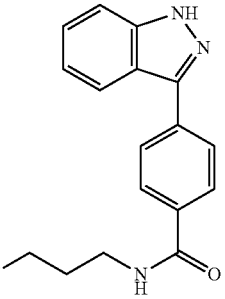 Product 7 on Scheme (A) | ND*) | 3.5 | ND |
| Ac-RPKRPTTLNLF (L-JIP Peptide) (SEQ ID NO: 16) | 2.9 | 0.423 | 6% at 50 μM |
| AcGRKKRRQRRRGGRPTTLNLGG (HIV TAT L-JIP peptide) (SEQ ID NO: 5) | ND | 90% inhibition at 50 μM | 6% at 50 μm |
| GGLNLTTPRGGRRRQRRKKRG-NH$_2$ (D-aminoacids) (HIV TAT D-JIP peptide) (SEQ ID NO: 6) | ND | 11% inhibition at 50 μM | 0% at 50 μm |

TABLE 1-continued

Comparative Results on Inhibition Using Compounds

| Compound | IC$_{50}$, μM | | |
|---|---|---|---|
| | Delfia Assay (Displacement of L-JIP1 peptide from JNK) | Kinase Activity Assay (JNK) | Kinase Activity Assay (p38) |
| Ac-RPTTLNLGG-OH (SEQ ID NO: 1) | 18 | 25% at 50 μM | |
| Ac-PTTLNLGG-OH (SEQ ID NO: 2) | ND*) | ND*) | ND |
| Ac-LNLGG-OH (SEQ ID NO: 3) | ND*) | ND*) | ND |
| Ac-LNL-OH | ND*) | ND*) | ND |

*)ND: In the Delfia Assay, no displacement up to 100 μM; in the Kinase Assay, no activity at 25 μM.

TABLE 2

Comparative Results on Inhibition Using Compounds of the Present Disclosure

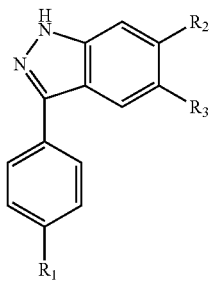

Linker & Peptide

| R$_1$ | R$_2$ | R$_3$ | IC$_{50}$ (μM) |
|---|---|---|---|
| H | H | NO$_2$ | 41% at 25 μM |
|  | H | H | 5.4 |
| 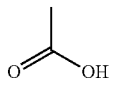 | H | H | 9.7 |
| 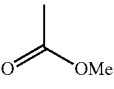 | H | H | 14 |
| 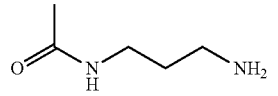 | H | 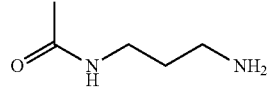 | 1.9 |
| 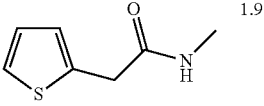 | H | H | 1.4 |
| 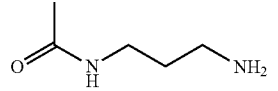 | H | H | 0.9 |

TABLE 2-continued

Comparative Results on Inhibition Using Compounds of the Present Disclosure

| R₁ | R₂ | R₃ | IC₅₀ (μM) |
|---|---|---|---|
| (acetamido-propyl-NHBoc) | H | H | 3.5 |
| (acetamido-propyl-NHBoc) | H | (thiophene-2-yl-acetamido-N-methyl) | 1.2 |
| (acetamido-propyl-NH-C(O)-quinoline-6-yl) | H | H | 5.7 |
| (acetamido-propyl-C(O)-NH-TEMPO) | H | H | 1.6 |
| (acetamido-pentyl-NH₂) | H | H | 6.3 |
| (acetamido-pentyl-NHBoc) | H | H | 2.3 |
| (acetamido-pentyl-NH-C(O)-naphthalen-2-yl) | H | H | 4.8 |
| (acetamido-pentyl-NH-C(O)-CH₂CH₂-adamantyl) | H | H | 2.2 |

TABLE 2-continued

Comparative Results on Inhibition Using Compounds of the Present Disclosure

| R₁ | R₂ | R₃ | IC₅₀ (μM) |
|---|---|---|---|
| (acetamido-pentyl-amide linked to 3,5-dimethyladamantane carboxamide) | H | H | 4.7 |
| (acetamido-pentyl-amide linked to adamantane-2-carboxamide) | H | H | 5.0 |
| (acetamido-pentyl-amide linked to 3-(4-nitrophenyl)adamantane-1-carboxamide) | H | H | 1.3 |
| (acetamido-pentyl-amide linked to 6,8-di-tert-butyl-4-oxo-4H-chromene-2-carboxamide) | H | H | 1.0 |
| (acetamido-pentyl-amide linked to retinoyl group) | H | H | 0.75 |

TABLE 2-continued

Comparative Results on Inhibition Using Compounds of the Present Disclosure

| R₁ | R₂ | R₃ | IC₅₀ (µM) |
|---|---|---|---|
| (acetamido-pentyl-amido-propyl-N-methylpiperazine) | H | H | 4.5 |

Figure 1B:
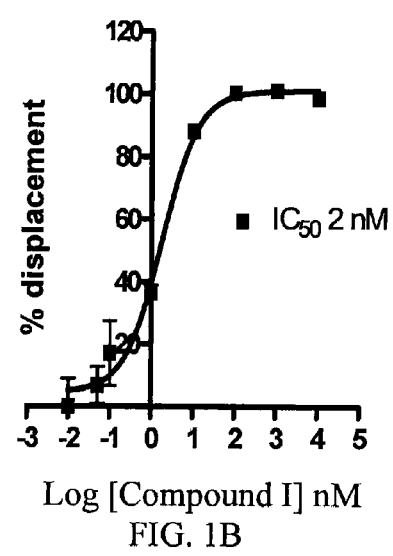
FIG. 1B illustrates kinase inhibition by a compound of the present disclosure.
Figure 1C:
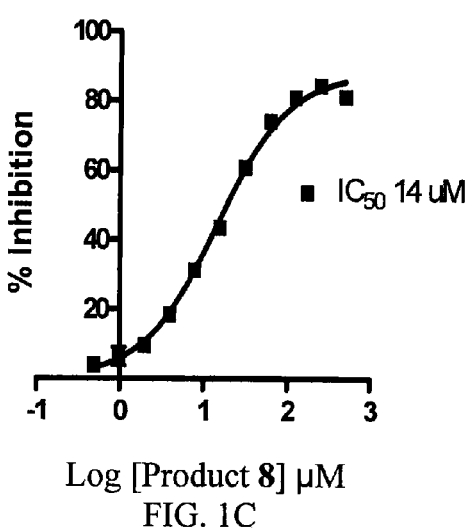
FIG. 1C illustrates kinase inhibition by a compound that is different from compounds of the present disclosure, which illustration is provided for the purposes of comparison.
Figure 1D:
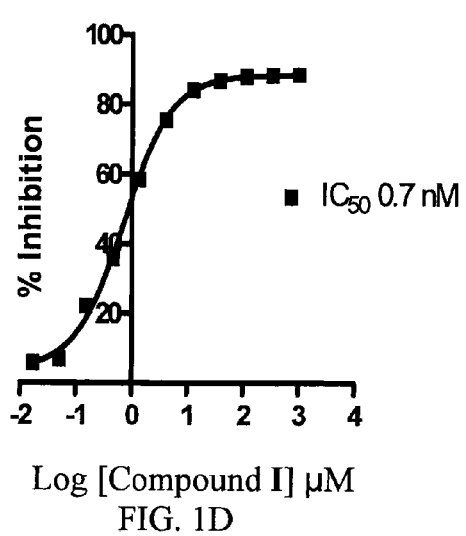
FIG. 1D illustrates kinase inhibition by a compound of the present disclosure.

FIGS. 1A-1D, 2A-2D, 3A, and 3B further exemplify embodiments of the present disclosure. FIGS. 1A and 1B illustrate kinase inhibition obtained in Delfia Assay for the peptide Ac-RPTTLNLGG—OH (SEQ ID NO:1) (FIG. 1A) and for compound I of the present disclosure (FIG. 1B). FIGS. 1C and 1D illustrate kinase inhibition obtained in Delfia Assay for the product 8 (FIG. 1C) and for compound I of the present disclosure (FIG. 1D). As can be seen, compound I is substantially more active as an inhibitor in both comparisons.

Figure 2A:
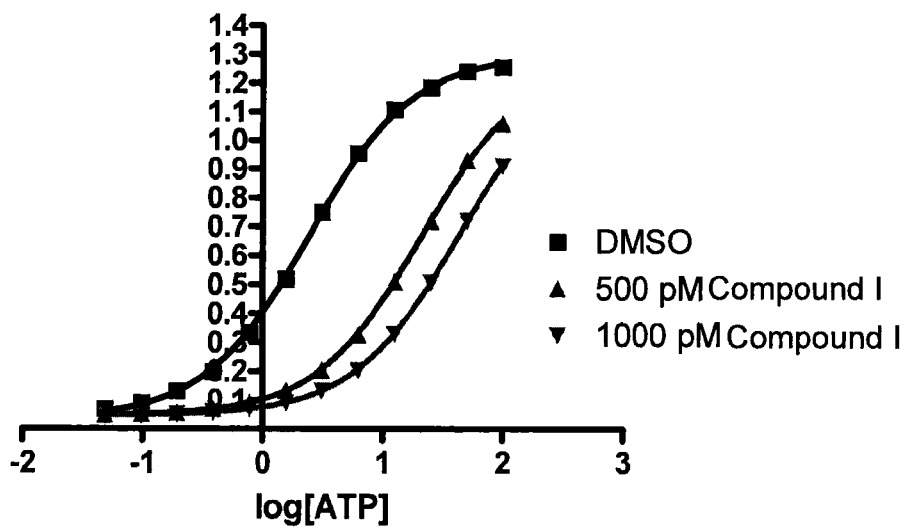
FIG. 2A provides the data on the ATP competition analysis for a compound of the present disclosure.
Figure 2B:
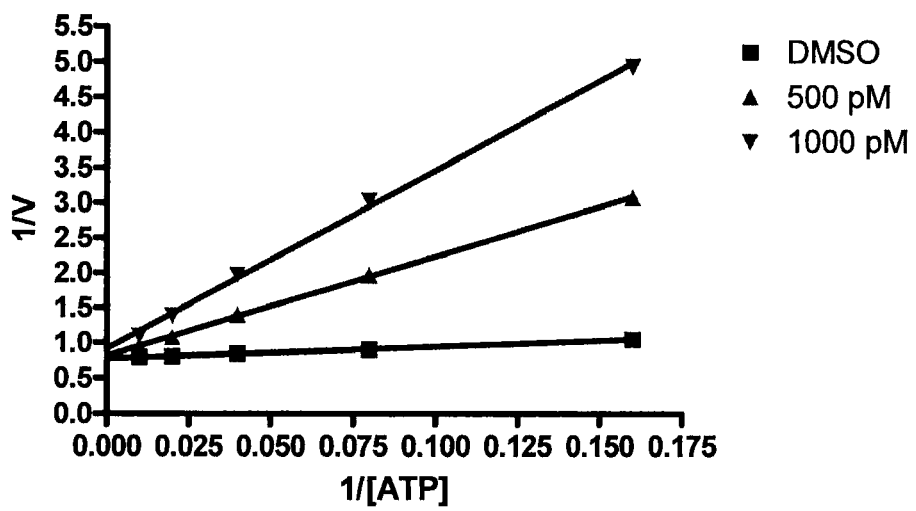
FIG. 2B provides further data on the ATP competition analysis for a compound of the present disclosure.
Figure 2C:
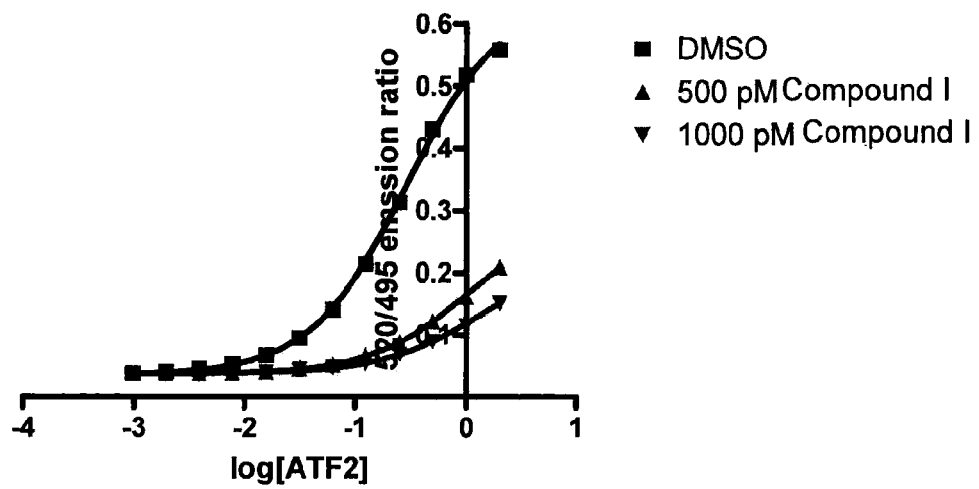
FIG. 2C provides the data on the ATF2 competition analysis for a compound of the present disclosure.
Figure 2D:
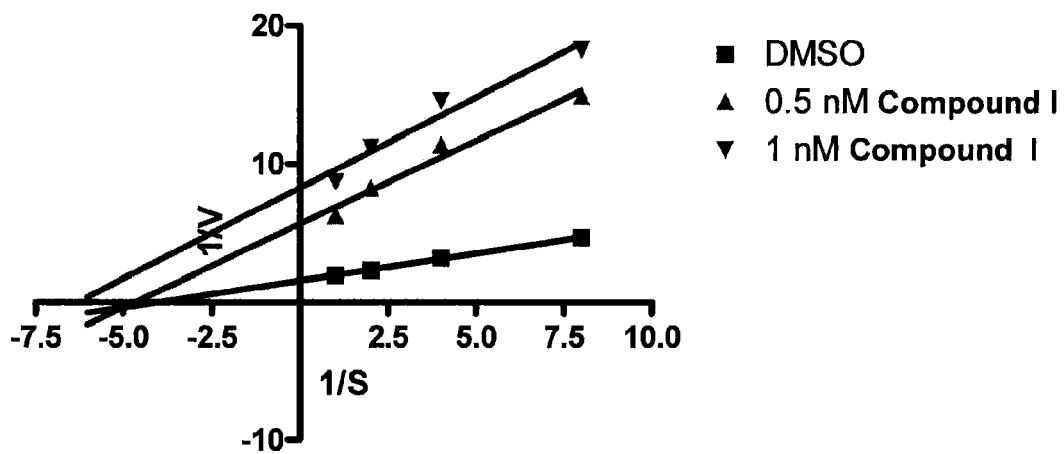
FIG. 2D provides further data on the ATF2 competition analysis for a compound of the present disclosure.
Figure 3A:
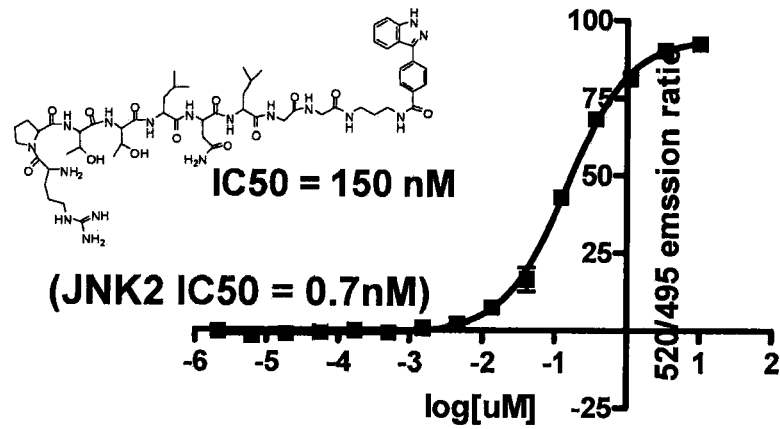
FIG. 3A provides the data on selectivity of a compound of the present disclosure relative to p38.
Figure 3B:
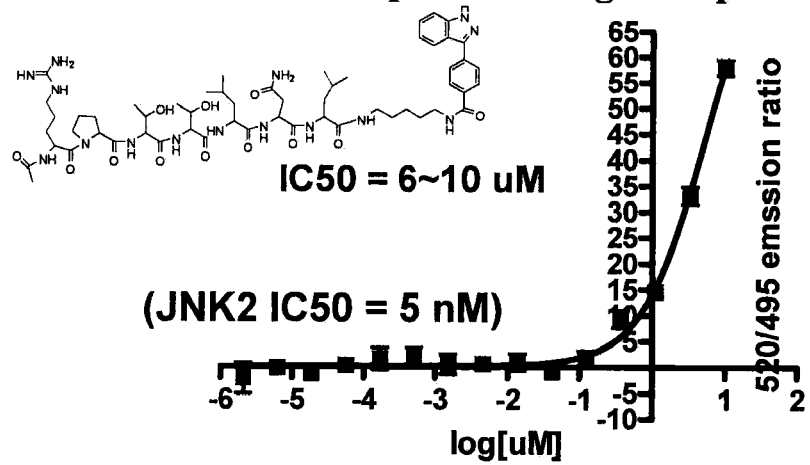
FIG. 3B provides the data on selectivity of another compound of the present disclosure relative to p38.

FIGS. 2A and 2B provide the data on the ATP competition analysis for Compound I, and FIGS. 2C and 2D the data on the ATF2 competition analysis for Compound I. These data demonstrate that Compound I is competitive, at least to some extent, in both sets of experiments. FIGS. 3A and 3B further demonstrate that both Compound I (FIG. 3A) and Compound IV (FIG. 3B) possess good selectivity relative to p38a.

Example 3

Design, Synthesis and Characterization of a Potent and Selective Dual ATP- and Substrate-Competitive Sub-nanomolar Bi-dentate JNK Inhibitor.

DELFIA Assay (dissociation enhanced lanthanide fluoro-immuno assay). To each well of 96-well streptavidin-coated plates (Perkin-Elmer) 100 µL of a 100 ng/ml solution of biotin-labeled pepJIP1 (Biotin-1c-KRPKRPTTLNLF (SEQ ID NO:18), where 1c indicates a hydrocarbon chain of 6 methylene groups) was added. After 1 hr incubation and elimination of unbound biotin-pepJIP1 by 3 washing steps, 87 µL of Eu-labeled anti-GST antibody solution (300 ng/ml; 1.9 nM), 2.5 µL DMSO solution containing test compound, and 10 µL solution of GST-JNK1 for a final protein concentration of 10 nM was added. After 1 hr incubation at 0° C., each well was washed 5 times to eliminate unbound protein and the Eu-antibody if displaced by a test compound. Subsequently, 200 µL of enhancement solution (Perkin-Elmer) was added to each well and fluorescence measured after 10 min incubation (excitation wavelength, 340 nm; emission wavelength, 615 nm). Controls include unlabeled peptide and blanks receiving no compounds. Protein and peptide solutions were prepared in DELFIA buffer (Perkin-Elmer).

LanthaScreen™ In vitro Kinase Assay. LanthaScreen™ assay platform from Invitrogen was utilized. The time-resolved fluorescence resonance energy transfer assay (TR-FRET) was performed in 384 well plates. Each well received JNK1 (100 ng/mL), ATF2 (200 nM), and ATP (1 µM) in 50 mM HEPES, 10 mM MgCl2, 1 mM EGTA and 0.01% Brij-35, pH 7.5 and test compounds. The kinase reaction was performed at room temperature for 1 hr. After this time, the terbium labeled antibody and EDTA were added into each well. After an additional hour incubation, the signal was measured at 520/495 nm emission ratio on a BMG Pherastar fluorescence plate reader.

In vitro Kinase Assay. BI77B8 was kept as a 10 mM solution in 10% DMSO. Serial dilutions containing 1% DMSO were prepared and BI77B8 was added at a ratio of 1:10 to each kinase reaction to obtain the indicated final concentrations. JNK kinase assays were performed with 50 ng per reaction of active JNK2α2 from Upstate/Millipore (Cat. No. 14-329) according to the recommendations of the manufacturer with the following changes: GST-c-Jun (1-79) was used as a substrate 1 ug per reaction[34]. The kinase reactions were performed at 30° C. for 20 minutes without Brij-35, and were stopped by addition of 2×Laemmli loading buffer and boiling for 3 minutes. The proteins were then separated on a mini gel and transferred to a PVDF membrane by wet blot. The membranes were dried and exposed to film.

Cell based assays for c-Jun phosphorylation. All cell culture media and supplements were from Life Technologies. The B16-F10 murine melanocyte cell line was purchased from ATCC and maintained according to manufacturers recommendations. At 48 hr prior to measuring phospho-c-jun levels, cells were transduced with BacMam GFP-c-Jun (1-79). BacMam preparation and transductions were performed as previously reported[35]. Briefly, the cells were grown in 10 cm dishes to approximately 75% confluence. The transduction was performed by adding 10% vol/vol BacMam virus stock in combination with Trichstatin A at a final concentration of 0.5 mM. The cells were incubated for 24 hrs. BacMam GFP-c-Jun (1-79) transduction efficiency, as determined by fluorescence microscopy, exceeded in general 80% of the cell population. All transductions were performed at a signal saturating MOI (at least 500 IU/cell). Following the transduction the cells were trypsinized and plated in white tissue culture treated 384 well plates at a density of 25000 cell per well in 32 ml assay medium (Opti-MEM®, supplemented with 0.1% charcoal/dextran-treated FBS, 100 U/mL penicillin and 100 mg/mL streptomycin, 0.1 mM non-essential amino acids, 1 mM sodium pyruvate, 25 mM HEPES pH 7.3, and lacking phenol red). After overnight incubation, cells were pretreated for 60 min with compound (indicated concentrations) followed by 30 min of stimulation with 2 ng/ml of TNF-□. The medium was then removed by aspiration and the cells were lysed by adding 20 ml of lysis buffer (20 mM TRIS-HCl pH 7.6, 5 mM EDTA, 1% NP-40 substitute, 5 mM NaF, 150 mM NaCl, 1:100 protease and phosphatase inhibitor mix, SIGMA P8340 and P2850 respectively). The lysis buffer included 2 nM of the terbium labeled anti-pc-Jun (pSer73) detection antibody (Life Technologies). After allowing the assay to equilibrate for 1 hour at room temperature, TR-FRET emission ratios were determined on a BMG Pherastar fluorescence plate reader (excitation at 340 nm, emission 520 nm and 490 nm; 100 ms lag time, 200 ms integration time, emission ratio=Em520/Em 490).

THP-1 Cell Assay for Inhibition of LPS-Induced TNF-□ and IL-1β Production. THP-1 cells (ATCC TIB 202, ATCC, Rockville, Md.) were maintained at 37° C., 5% CO2 in 10% fetal bovine serum (FBS)/RPMI 1640 medium. The day of the assay, $2 \times 10^6$ cells were resuspended in 1 mL of 3% FBS/RPMI 1640 medium and plated in a 12-well plate. BI87G9 and D-JNK1, 12.5 μM each, or DMSO vehicle was added to the cell mixture and allowed to preincubate for 60 min at 37° C., 5% CO2, prior to stimulation with LPS (Sigma L6529, from E. coli serotype 055:B5; 1 μg/mL final). LPS stimulation was allowed to proceed for 5 hr at 37° C., 5% CO2. TNF-α and IL-1β production was measured directly from cell culture medium by a commercially available sandwich immunoassay developed by Meso Scale Discovery (Meso Scale no. K15025B-1, Gaithersburg, Md.). Levels of TNF-□ and IL-1β in the cell culture medium were determined using a Meso Scale Discovery Sector Imager 2400 according to the manufacturer's instructions.

Molecular Modeling. Computational docking studies were performed with GOLD 2.1 (The Cambridge Crystallographic Data Centre, Cambridge, UK)[36,37] and analyzed with Sybyl (Tripos, St. Louis). Molecular surfaces were generated with MOLCAD[33]. The X-ray coordinates ofJNK1/pepJIP1/SP600125 (PDB-ID 1UKI) were used to dock the compounds. Peptide and BI77B1 and bi-dentate BI77B8 poses reported in FIG. 4 of the manuscript correspond to those obtained directly from the X-ray coordinates.

Glucose Tolerance Test. 26-week-old male NONcNZO10/LtJ mice from Harlan (Jackson Labs, Bar Harbor, Me. 04609 USA) were dosed intraperitoneally (i.p.) with 25 mg/kg of BI87G9 and D-JNK1 daily for four days. Mice were fasted 16 hours before i.p. administration of 2 g/kg D-glucose. Blood samples were taken at designated time points and blood glucose levels were measured using a hand-held glucose meter (OneTouch Ultra, LifeScan, a Johnson & Johnson company, UK).

Chemistry. All anhydrous solvents were commercially obtained and stored in Sure-seal bottles under nitrogen. All other reagents and solvents were purchased as the highest grade available and used without further purification. Thin-layer chromatography (TLC) analysis of reaction mixtures was performed using Merck silica gel 60 F254 TLC plates, and visualized using ultraviolet light. $^1$H NMR data were collected using a 300 MHz Varian instrument and recorded in deuteron-chloroform (CDCl$_3$) or dimethyl sulfoxide-d$_6$ (DMSO-d$_6$). Chemical shifts (δ) are reported in parts per million (ppm) referenced to $^1$H (Me$_4$Si at 0.00). Mass spectral data were acquired on a Shimadzu LCMS-2010EV for low resolution, and on an Agilent ESI-TOF for high resolution and low resolution. Purity of compounds was determined using a Waters HPLC. List of Abbreviations: equivalent (eqv), high performance liquid chromatography (HPLC), liquid chromatography/mass spectrometry (LC/MS), room temperature (rt). Purity of compounds was obtained in a HPLC Breeze from Waters Co. using an Atlantis T3 3 μm 4.6×150 mm reverse phase column. Following the scheme reported in FIG. 4: compound 1 (indazole) was commercially available, which was iodinated according to the reported procedures.

Synthesis of 3-iodo-1-((2-(trimethylsilyl)ethoxy)methyl)-1H-indazole (3): To a solution of compound 2 (1.22 g, 5 mmol) in DMF (10 mL) was added NaH (220 mg, 5.50 mmol) in three portions at 0° C. under nitrogen atmosphere. The reaction mixture was stirred at the same temperature for 30 min then SEM-Cl (0.9 mL, 5 mmol) was added dropwise to it. The resulting reaction mixture was stirred at 0° C. for 1 h then at room temperature for 4 h. The reaction mixture was quenched with cold water (100 mL) followed by extraction with ether (3×100 mL). The combined organic layers were washed with water (100 mL) and brine (100 mL), dried (MgSO$_4$), and concentrated in vacuo. The residue was chromatographed over silica gel (5% ethyl acetate in hexane) to afford the colorless oil 3 (1.68 g, 90%). $^1$H NMR (300 MHz, CDCl$_3$) δ-0.07 (s, 9 H), 0.88 (t, J=7.2 Hz, 2 H), 3.57 (t, J=7.5 Hz, 2 H), 5.72 (s, 2 H), 7.27 (d, J=8.2 Hz, 1 H), 7.44-7.58 (m, 3 H); HRMS calcd for C$_{13}$H$_{19}$IN$_2$OSi 374.0311, found 374.0312.

Synthesis of methyl-4-(1-((2-(trimethylsilyl)ethoxy)methyl-1H-indazol-3y1)benzoate (4): A mixture of 3 (374 mg, 1 mmol), 4-methoxycarbonylphenyl boronic acid (271 mg, 1.5 mmol), Pd(dppf)Cl$_2$ (82 mg, 0.1 mmol), saturated aqueous Na$_2$CO$_3$ solution (4 mL), in ethanol (1 mL) and toluene (10 mL) was stirred at 80° C. for 12 h. Upon completion of the reaction (TLC), the reaction mixture was extracted with CH$_2$Cl$_2$ (3×50 mL). The combined organic layers were washed with water (50 mL), and brine (50 mL), dried (MgSO$_4$), and concentrated in vacuo. The residue was chromatographed over silica gel (5 to 10% ethyl acetate in hexane) to yield the pure product 4 (295 mg, 77%). $^1$H NMR (300 MHz, CDCl$_3$) δ-0.05 (s, 9H), 0.88 (t, J=8.4 Hz, 2 H), 3.60 (t, J=8.4 Hz, 2 H), 3.95 (s, 3 H), 5.81 (s, 2 H), 7.28 (t, J=7.2 Hz, 1 H), 7.42 (t, J=7.5 Hz, 1 H), 7.62 (d, J=8.4 Hz, 1 H), 7.85-8.22 (m, 5 H); EIMS m/z 383 (M+H)$^+$, 325, 267, 265, 149, 121, 83; HRMS calcd for C$_{21}$H$_{27}$N$_2$O$_3$Si 383.1785, found 383.1784.

Synthesis of 4-(1-((2-(trimethylsilypethoxy)methyl)-1H-indazol-3-y)benzoic acid (5): To a solution of compound 4 (282 mg, 0.738 mmol) in THF (6 mL) and methanol (1 mL) was added LiOH solution (177 mg, 7.380 mmol) in water (2 mL). The resulting reaction mixture was stirred at room temperature for 18 h. The reaction mixture was acidified with 1 N HCl followed by extraction with CH$_2$Cl$_2$ (3×50 mL). The combined organic layers were dried (MgSO$_4$) and concentrated in vacuo. The residue was chromatographed over silica gel (20 to 30% ethyl acetate in hexane) to afford the acid 5 (195 mg, 90%). $^1$H NMR (300 MHz, CDCl$_3$) δ-0.06 (s, 9 H), 0.92 (t, J=8.4 Hz, 2 H), 3.64 (t, J=8.4 Hz, 5.83 (s, 2 H), 7.32 (t, J=7.2 Hz, 1H), 7.49 (t, J=7.5 Hz, 1 H), 7.66 (d, J=8.4 Hz, 1 H), 8.06 (d, J=8.4 Hz, 1 H), 8.12 (d, J=8.7 Hz, 2 H), 8.27 (d, J=8.1 Hz, 2 H); EIMS m/z 369 (M+H)$^+$, 339, 311, 251, 149, 121, 99, 55; HRMS calcd for C$_{20}$H$_{25}$N$_2$O$_3$Si 369.1629 (M+H), found 369.1627.

Synthesis of tert-butyl-3-(4-(1-((2-(trimethylsilypethoxy) methyl-1H-indazol-3-yl)-benzamido)propylcarbamate (6): To a solution of 5 (155 mg, 0.421 mmol) in DMF (3 mL) were added EDC (96 mg, 0.505 mmol), HOBt (68 mg, 0.505 mmol), DIEA (0.19 mL, 1.052 mmol), and mono-Boc-1,3-diamino propane (82 mg, 0.463 mmol). The reaction mixture was stirred at room temperature for 16 h. Upon completion the reaction mixture was diluted with water (40 mL) followed by extraction with ethyl acetate (3×40 mL). The combined organic layers were washed with saturated NaHCO$_3$ solution (2×30 mL), water (3×30 mL), and brine (30 mL) successively, dried (MgSO$_4$), and concentrated in vacuo. The residue was chromatographed over silica gel (50% ethyl acetate in hexane) to give the pure product 6 (175 mg, 79%). $^1$H NMR (300 MHz, CDCl$_3$) δ-0.063 (s, 9 H), 0.91 (t, J=8.7 Hz, 2 H), 1.47 (s, 9 H), 1.74 (quintet, J=5.7 Hz, 2 H), 3.29 (q, J=6 Hz, 2 H), 3.55 (q, J=6 Hz, 2 H), 3.63 (t, J=8.4 Hz, 2 H), 4.95 (br s, 1 H, NH), 5.80 (s, 2 H), 7.30 (d, J =7.2 Hz, 1 H), 7.47 (t, J=7.2 Hz, 1 H), 7.63 (d, J=8.4 Hz, 1 H), 7.98-8.12 (m, 5 H); HRMS calcd for C$_{28}$H$_{40}$N$_4$O$_4$Si 524.2819, found 524.2817.

Synthesis of tert-butyl-3-(4-(1H-indazol-3-yl)benzamido) propylcarbamate (7): To a solution of 6 (76 mg, 0.141 mmol) in THF (5 mL) was added TBAF (0.7 mL, 1 M solution in THF) at room temperature. The reaction mixture was refluxed for 10 h. Upon completion the reaction mixture was partitioned between dichloromethane (40 mL) and water (30 mL). The organic layer was washed with water (30 mL) and brine (30 mL), dried (MgSO4), and concentrated in vacuo. The residue was chromatographed over silica gel (80% ethyl acetate in hexane) to give the pure product 7(42 mg, 76%). $^1$H NMR (300 MHz, DMSO-d$_6$) δ 1.38 (s, 9 H), 1.65 (quintet, J=6.6 Hz, 2 H), 3.01 (q, J=6.3 Hz, 2 H), 3.30 (q, J=6.3 Hz, 2 H), 6.83 (br s. NH), 7.24 (t, J=7.8 Hz, 1 H), 7.42 (t, J=6.9 Hz, 1 H), 7.62 (d, J=8.4 Hz, 1 H),7.99 (d, J=8.7 Hz, 2 H), 8.05- 8.15 (m, 3 H), 8.52 (t, J=5.4 Hz, 2 H), EIMS m/z 395 (M+H)$^+$, 339, 295, 221, 83; HRMS calcd for C$_{22}$H$_{27}$N$_4$O$_3$ 395.2078 (M+H), found 395.2077.

Synthesis of N-(3-aminopropyl)-4-(1H-indazol-3-yl)benzamide (BI-77B1): To a solution of compound 7(21 mg, 0.053 mmol) in CH$_2$Cl$_2$ (2 mL) was added TFA (0.5 mL). The resulting reaction mixture was stirred at room temperature for 2 h. TFA and dichloromethane were removed in vacuum to give BI77B 1. This compound was used for the next step without further purification.

Synthesis of N$^1$-(1-(4-(1H-indazol-3-yl) phenyl-16-methyl-1,7,10,13 -tetraoxo-2,6,9,12-tetraazaheptadecan-14-yl) -2(2-(2-(2-(1-(2-amino-5-gu anidinopentanoyl) pyrolidine-2- carboxamido) -3-hydroxybutanamido)-3-hydroxybutanamido)-4-methylpentanamido)-succinamide (BI-77B8): To a solution of BI77B1 (15 mg, 0.051 mmol) in DMF (2 mL) were added EDC (10 mg, 0.051 mmol), HOBt (6 mg, 0.051 mmol), DIEA (0.5 mL), and Boc-Arg(Pbf) -Pro-Thr (otbu)-Thr(Otbu)-Leu-Asn(trt)-Leu-Gly-Gly-OH (SEQ ID NO:1) (70 mg, 0.042 mmol) at room temperature. The reaction mixture was stirred at 50° C. for 16 h. Afte completion of the reaction, DMF and DIEA were removed in vacuo to give the protected compound. The crude residue was directly treated with TFA (1 mL) and H$_2$O (0.2 mL) for 3 h. The final product was obtained by HPLC purification. $^1$NMR (300 MHz, CD$_3$OD) δ0.74-0.79 (m, 12 H), 1.25-2.20 (m, 24 H), 2.42-2.82 (m, 2 H), 3.01-3.94 (m, 10 H), 4.10-4.65 (m, 8 H), 7.15 (br, NH), 7.34-7.45 (m, 4 H), 7.50 (br, NH), 7.61 (d, J =8.4 Hz, 2 H), 7.74 (d, J =7.8 Hz, 2 H), 7.89 (d, J =8.4 Hz, 1 H), 7.95 (br, NH); EIMS m/z 1204 (M+H)$^+$, 1051, 860, 602, 450, 295, 136, 130, 108; HRMS calculated for C$_{56}$H$_{86}$N$_{17}$O$_{13}$1204.6585 (M+H), found 1204.6572.

Similarly, the synthesis of BI87G9 was obtained by coupling methyl-4-(4-(1H-indazol-3-yl)benzamido) butanoate (analogue to compound BI77B1 but with a free carboxylic acid in lieu of the free amine) was coupled with a peptide of D-amino acids on resin using standard peptide coupling conditions. After coupling reaction complete, resin was removed with the treatment of TFA. Final compound was purified by rev phase HPLC. The compound was dried and checked purity again with HPLC (purity was >93%) and analyzed with MALDI-mass.

Although the disclosure has been described with reference to the above examples, it will be understood that modifications and variations are encompassed within the spirit and scope of the disclosure. Accordingly, the disclosure is limited only by the following claims.

What is claimed is:

1. A compound of formula I:

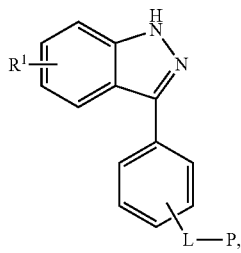

(I)

or a pharmaceutically acceptable salt thereof, wherein:
R[1] is hydrogen, straight-chained alkyl, branched alkyl, halogen, nitro, or NHC(O)CH$_2$C$_4$H$_3$S;

5. The compound of formula I of claim 4, wherein the compound of formula I has formula II:

(SEQ ID NO: 11)

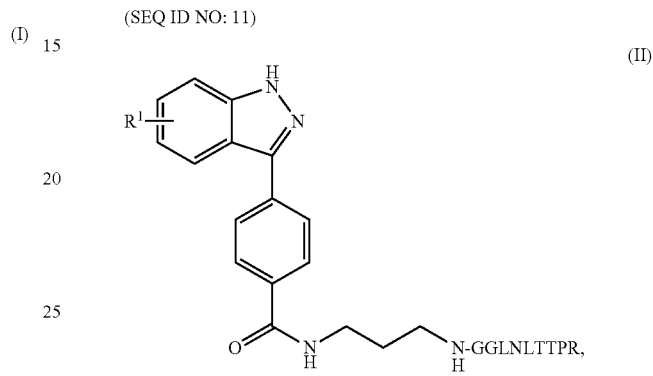

(II)

or has formula III:

(SEQ ID NO: 6 (D amino acids))

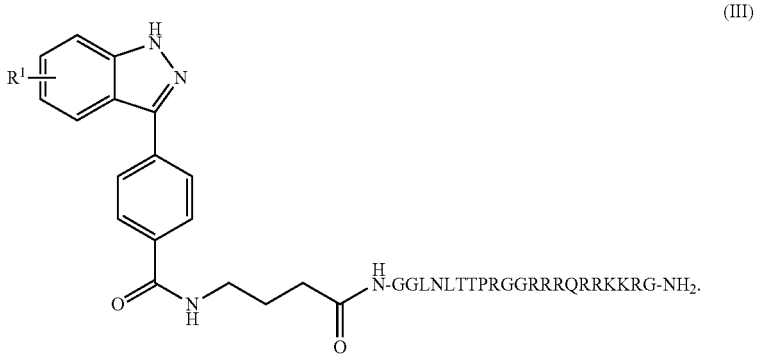

(III)

L is a linking moiety selected from the group consisting of:
(a) —CONH—(CH$_2$)$_n$—NH—, (b) —CONH—(CH$_2$)$_n$—NHCO—, (c) —CONH—(CH$_2$)$_n$—CONH—, (d) —(CH$_2$)$_n$—, (e) —O—(CH$_2$)$_n$—O—, (f) —(CH$_2$)-phenylene-, and (h) —NHSO$_2$—(CH$_2$)$_n$CONH—, wherein n is an integer between 2 and 8; and P is a peptide consisting of the sequence selected from the group consisting of RPTTLNL (SEQ ID NO:4), N-myristoilated RPTTLNL (SEQ ID NO:4), and GGLNLTTPRGGRRRQRRKKRG (SEQ ID NO:6).

2. The compound of formula I of claim 1, wherein the compound binds to a JNK kinase docking site.

3. The compound of formula I of claim 1, wherein L is —CONH—(CH$_2$)$_n$—NH—; and P is a peptide consisting of the sequence selected from RPTTLNL (SEQ ID NO:4), and GGLNLTTPRGGRRRQRRKKRG (SEQ ID NO:6).

4. The compound of formula I of claim 3, wherein R[1] is hydrogen or straight chain alkyl; and L is —CONH—(CH$_2$)$_3$—NH—.

6. A pharmaceutical composition comprising the compound of formula I of claim 1 or the compound of formula II or formula III of claim 5, and a pharmaceutically acceptable carrier.

7. The composition of claim 6, further comprising an additional compound selected from the group consisting of: (1) an estrogen receptor modulator, (2) an androgen receptor modulator, (3) retinoid receptor modulator, (4) a cytotoxic agent, (5) an antiproliferative agent, (6) a prenyl-protein transferase inhibitor, (7) an HMG-CoA reductase inhibitor, (8) an HIV protease inhibitor, (9) a reverse transcriptase inhibitor, (10) another angiogenesis inhibitor, and (11) a PPAR-gamma agonist.

8. A method of treating retinal vascularization, comprising administering to a subject a therapeutically effective amount of the pharmaceutical composition of claim 6.

9. A method of treating diabetic retinopathy, comprising administering to a subject a therapeutically effective amount of a pharmaceutical composition of claim 6.

10. A kit comprising a packaging material and the pharmaceutical composition of claim 6 contained within the packaging material, wherein the packaging material comprises a label which indicates that the composition can be used for treating a disorder, disease, or pathology in a subject in need thereof.

* * * * *